(12) United States Patent
Tuck et al.

(10) Patent No.: US 6,243,657 B1
(45) Date of Patent: Jun. 5, 2001

(54) METHOD AND APPARATUS FOR DETERMINING LOCATION OF CHARACTERISTICS OF A PIPELINE

(75) Inventors: Alan Tuck, Northumberland; Gary Brayson, Tyne And Wear, both of (GB); Mario B. Ignagni, Arden Hills; Alan B. Touchberry, St. Louis Park, both of MN (US); Donald William Anderson, Newcastle-Upon Tyne (GB); Stephen James Glen, Tyne & Wear (GB); James Michael Alexander Gilman, Newcastle Upon-Tyne (GB)

(73) Assignee: PII North America, Inc., Houston, TX (US)

( * ) Notice: Subject to any disclaimer, the term of this patent is extended or adjusted under 35 U.S.C. 154(b) by 0 days.

(21) Appl. No.: 08/996,504

(22) Filed: Dec. 23, 1997

(51) Int. Cl.$^7$ .................................................. G01C 9/00
(52) U.S. Cl. .................... 702/150; 702/176; 702/142; 700/186; 700/187; 700/188; 700/189; 700/190; 700/204; 701/213; 701/214; 701/215; 73/865.68; 324/207.13; 324/220
(58) Field of Search .................................. 702/150, 176, 702/142; 700/186–190, 204; 701/213, 214, 215; 73/865.08; 324/207.13, 220

(56) References Cited

U.S. PATENT DOCUMENTS

| 2,262,934 | 11/1941 | Hering ................................ 33/205.5 |
| 2,940,302 | 6/1960 | Scherbatskoy ........................ 73/40.5 |

(List continued on next page.)

FOREIGN PATENT DOCUMENTS

| 1199169 | 1/1986 | (CA) . |
| 1216921 | 1/1987 | (CA) . |
| 1224874 | 7/1987 | (CA) . |
| 1204487 | 5/1991 | (CA) . |
| 1284426 | 5/1991 | (CA) . |
| 1286772 | 7/1991 | (CA) . |
| 1303722 | 6/1992 | (CA) . |
| 2085048 | 12/1992 | (CA) . |
| 1325476 | 12/1993 | (CA) . |
| 1327403 | 3/1994 | (CA) . |
| 2133930 | 10/1994 | (CA) . |
| 2184327 | 8/1996 | (CA) . |
| 3 438 719 | 4/1986 | (DE) . |

(List continued on next page.)

OTHER PUBLICATIONS

Hadfield, M.J., "Location, Navigation and Survey–Adaptability of High Precision ESG Inertial Systems in the 1980's", Honeywell, Inc., IEEE, 1978.

(List continued on next page.)

Primary Examiner—Kamini Shah
(74) Attorney, Agent, or Firm—Akin, Gump, Strauss, Hauer & Feld, LLP

(57) ABSTRACT

A pipeline inspection and defect mapping system includes a pig having an inertial measurement unit and a pipeline inspection unit for recording pig location and defect detection events, each record time-stamped by a highly precise onboard clock. The system also includes several magloggers at precisely known locations along the pipeline, each containing a fluxgate magnetometer for detecting the passage of the pig along the pipeline and further containing a highly precise clock synchronized with the clock in the pig. The locations of the various magloggers are known in a north/east/down coordinate system through a differential global positioning satellite process. Finally, a postprocessing off-line computer system receives downloaded maglogger, inertial measurement, and odometer data and through the use of several Kalman filters, derives the location of the detected defects in the north/east/down coordinate frame. Consequently, a task of identifying sites for repair activity is much simplified.

32 Claims, 9 Drawing Sheets

U.S. PATENT DOCUMENTS

| | | | |
|---|---|---|---|
| 3,238,448 | 3/1966 | Wood et al. | |
| 3,460,028 | 8/1969 | Beaver et al. | 324/37 |
| 3,495,546 | 2/1970 | Brown et al. | 104/155 |
| 3,769,711 | 11/1973 | Flournoy et al. | |
| 3,786,684 | 1/1974 | Wiers et al. | 73/432 R |
| 3,810,834 | 5/1974 | Evans | 73/67.8 S |
| 3,828,867 | 8/1974 | Elwood | 175/45 |
| 3,845,569 | 11/1974 | Otte et al. | 33/312 |
| 3,882,606 | 5/1975 | Kaenel et al. | 33/174 L |
| 3,896,412 | 7/1975 | Rohr | 340/15.5 BA |
| 3,960,006 | 6/1976 | Smith | 73/67.8 S |
| 3,964,171 | 6/1976 | Gambini et al. | 33/178 E |
| 4,052,686 | 10/1977 | Schmitz | 336/65 |
| 4,071,959 | 2/1978 | Russell et al. | 33/312 |
| 4,162,635 | 7/1979 | Triplett et al. | 73/623 |
| 4,298,280 | 11/1981 | Harney | 356/5 |
| 4,468,863 | 9/1984 | Van Steenwyk | 33/304 |
| 4,481,816 | 11/1984 | Prentice | 73/432 R |
| 4,491,018 | 1/1985 | Stringer et al. | |
| 4,524,526 | 6/1985 | Levine | 33/312 |
| 4,559,713 | 12/1985 | Ott et al. | 33/302 |
| 4,560,928 | 12/1985 | Hayward | 324/172 |
| 4,598,585 | 7/1986 | Boxenhorn | 73/505 |
| 4,609,869 | 9/1986 | Metcalf | |
| 4,641,529 | 2/1987 | Lorenzi et al. | 73/601 |
| 4,655,085 | 4/1987 | Tomizawa et al. | 73/638 |
| 4,665,734 | 5/1987 | Joet | 73/622 |
| 4,715,128 | 12/1987 | Cummings et al. | 33/544 |
| 4,717,875 | 1/1988 | Lara | 324/220 |
| 4,744,246 | 5/1988 | Busta | 73/204 |
| 4,747,317 | 5/1988 | Lara | 73/865.8 |
| 4,756,229 | 7/1988 | Drakeley | 91/1 |
| 4,757,716 | 7/1988 | Nottingham et al. | 73/623 |
| 4,799,391 | 1/1989 | Lara | 73/865.8 |
| 4,825,711 | 5/1989 | Jensen et al. | |
| 4,835,876 | 6/1989 | Petermann et al. | 33/313 |
| 4,920,655 | 5/1990 | Van Steenwyk | 33/304 |
| 4,945,775 | 8/1990 | Adams et al. | 73/865.8 |
| 4,954,837 | 9/1990 | Baird et al. | 342/458 |
| 4,970,682 | 11/1990 | Beckwith, Jr. et al. | 364/900 |
| 4,987,684 | 1/1991 | Andreas et al. | 33/304 |
| 5,060,175 | 10/1991 | Cubalchini et al. | 364/559 |
| 5,166,789 | 11/1992 | Myrick | 358/109 |
| 5,331,578 | 7/1994 | Stieler | 364/571.01 |
| 5,363,700 | 11/1994 | Joly et al. | 73/504 |
| 5,565,633 | 10/1996 | Wernicke | 73/865.3 |
| 5,640,780 | 6/1997 | Kermabon | 33/544 |
| 5,657,547 | 8/1997 | Uttecht et al. | 33/304 |
| 5,659,142 | 8/1997 | Lima et al. | 73/865.3 |
| 5,739,420 | 4/1998 | Peterson | 73/40.5 |
| 5,742,053 | 4/1998 | Rekunyk | 250/338.5 |
| 5,752,513 | 5/1998 | Acker et al. | 128/653.1 |

FOREIGN PATENT DOCUMENTS

| | | |
|---|---|---|
| 0 077 504 | 4/1983 | (EP) |
| 0 181 012 | 5/1986 | (EP) |
| 0 236 614 | 9/1987 | (EP) |
| 0 294 811 | 12/1988 | (EP) |
| 2 086 055 | 5/1982 | (GB) |
| 2 126 722 | 3/1984 | (GB) |
| WO85/05652 | 12/1985 | (WO) |
| WO88/05113 | 7/1988 | (WO) |

OTHER PUBLICATIONS

Stankoff, Alain, "Underwater Survey Using An Inertial Navigation System", Intersub Developpement, and R.A. R. Tait, Ferranti, Ltd., 1977.

Necsulescu, D.S., Sasiadek, J.Z., Kim, B., and Green, D.N., "Fusion of Inertial and Kinematic Navigation Systems for Autonomous Vehicles", Honeywell, Inc., IEEE, 1993.

Julliere, M., Marce, L., and Perrichot, H., "A Guidance System for a Vehicle Which has to Follow A Memorized Path", Honeywell, Inc., (Proceeding of the 2nd International Conference on Automated Guided Vehicle Systems.

Borenstein, J. And Feng, L., "Gyrodometry: A New Method for Combining Data from Gyros and Odometry in Mobile Robots", Honeywell, IEEE, 1996.

Mueller, C.E. and Adams, Gary, "Laser Gyro Land Navigation System Performance Predictions and Field Results", 1984.

Gas Pipeline Technological Research Gives Lower Costs and Greater Security, The Institute of Petroleum, Petroleum Review Apr. 1987, pp. 17, 19, 21, 22.

Clever Pig Roots Through Pipes, The Institute of Petroleum, Petroleum Review Nov. 1989, p. 557.

Pipeline Safety and Leak Detection, PD–vol. 19, The American Society of Mechanical Engineers, A Review of In–Line Inspection Capabilities, J.F. Kiefner, et al., pp. 29–40.

Inspection Pig Systems for Offshore Pipeline, Nippon Kokan Technical Report, Overseas No. 39 (1983), pp. 113–119.

Defect Location and Sizing in a Transmission Pipeline is No Easy Task, vol. 88, May 7, 1990.

Three Good Reasons Why Flawsonic Should be Your Pipeline Wall–Thickness Measurement Service; TDW Pipeline Surveys, vol. 88, Sep. 3, 1990.

Defect Location and Sizing in a Transmission Pipeline is No Easy Task, vol. 88, Aug. 20, 1990.

Pipeline Geometry Pigging: Application of Strapdown Ins, Todd R. Porter et al., 1990 IEEE, pp. 353–358.

British Gas Has Seamless Pipe Inspection Program, Lawrence Jackson et al., Technology, Sep. 9, 1987, Oil & Gas Journal, pp. 147–148, 150, 152, 155–156.

Canadian Operator Details Internal Inpection Program, Gary C. Robinson, Technology, Jun. 3, 1985, Oil & Gas Journal, pp. 55–59.

On–Line Measurement of the Microstructure and Mechanical Properties of Steel, J.F. Busiere, Materials Evaluation/44/Apr. 1986, pp. 560–567.

PCT/ISA/210 International Search Report, second sheet & continuation of second sheet, Jun. 17, 1999.

FIG. 9

| SOLDA. CIRC. | DISTANC. RELATIVA (metros) | DISTANC. ABSOLUTA (metros) | INT/EXT | COMMENT | PROFUND MAXIMA % | LON AX. (mm) | FER | ORIENT (ho:min) | GPS CO-ORDINATES Longitude ° ' " | | | GPS CO-ORDINATES Latitude ° ' " | | | Altitude (metros) |
|---|---|---|---|---|---|---|---|---|---|---|---|---|---|---|---|
| 1 | 0.0 | 0.0 | | | | | | | | | | | | | 512.3 |
| 1 | 0.0 | 0.1 | | LAUNCH | | | | 12:00 | 69 | 46 | 12.17 | 33 | 27 | 8.12 | |
| 1 | 1.1 | 1.2 | | 2 IN OFFTAKE-WELDOLET | | | | 12:00 | | | | | | | |
| 1 | 2.2 | 2.3 | | 2 IN OFFTAKE-WELDOLET | | | | 12:00 | | | | | | | |
| 1 | 3.2 | 3.3 | | 2 IN OFFTAKE-WELDOLET | | | | 06:00 | | | | | | | 516.3 |
| 1 | 3.3 | 3.4 | | 2 IN OFFTAKE-WELDOLET | | | | | 69 | 46 | 9.12 | 33 | 27 | 9.11 | |
| 2 | 4.3 | 4.4 | | | | | | | | | | | | | |
| 2 | 1.3 | 5.7 | | BALL VALVE | | | | | | | | | | | 518.1 |
| 2 | 2.4 | 6.8 | | | | | | | 69 | 46 | 7.11 | 33 | 27 | 11.12 | |
| 3 | 2.3 | 9.1 | | 8 IN OFFTAKE-SWEEPOLET | | | | 12:00 | | | | | | | 517.9 |
| 5 | 3.4 | 10.2 | | | | | | | 69 | 46 | 3.22 | 33 | 27 | 12.55 | |
| 5 | 0.9 | 11.1 | | 14 IN OFFTAKE-FORGED | | | | 03:00 | | | | | | | 518.2 |
| 10 | 1.9 | 12.1 | | | | | | | 69 | 46 | 1.99 | 33 | 27 | 14.15 | |
| 10 | 0.5 | 12.6 | | 1.0 IN OFFTAKE-WELDOLET | | | | 12:00 | | | | | | | |
| 10 | 1.1 | 13.2 | | 1.0 IN OFFTAKE-WELDOLET | | | | 12:00 | | | | | | | |
| 20 | 2.0 | 14.1 | | JOINT-INSULATED | | | | | | | | | | | 518.3 |
| 20 | 0.9 | 15.0 | | | | | | | 69 | 46 | 1.01 | 33 | 27 | 15.55 | |
| 25 | 1.2 | 15.3 | | | | | | | 69 | 45 | 0.22 | 33 | 27 | 16.21 | 518.4 |
| 30 | 0.8 | 16.1 | | | | | | | 69 | 45 | 59.13 | 33 | 27 | 17.93 | 518.5 |
| 40 | 27.2 | 43.3 | | DEFECT | | | | | 69 | 45 | 59.08 | 33 | 27 | 18.11 | 519.5 |
| 50 | 22.4 | 65.7 | | | | | | | 69 | 45 | 58.12 | 33 | 27 | 18.99 | 521.2 |
| 60 | 0.4 | 66.1 | | | | | | | 69 | 45 | 58.11 | 33 | 27 | 19.07 | 522.3 |
| 60 | 8.2 | 74.3 | | BEND-COLD OVER | | | | | | | | | | | |
| 70 | 16.5 | 82.6 | | | | | | | 69 | 45 | 56.01 | 33 | 27 | 19.06 | 523.1 |
| 70 | 1.9 | 84.5 | | BEND-COLD UNDER | | | | 06:00 | | | | | | | |
| 70 | 12.0 | 94.6 | | | | | | | | | | | | | |
| 80 | 19.6 | 102.2 | | FULL CIRC FITTING | | | | | 69 | 45 | 55.12 | 33 | 27 | 21.24 | 522.3 |
| 80 | 3.0 | 105.2 | | RIVER CROSSING | | | | | | | | | | | |
| 80 | 32.2 | 134.4 | | NWT 0.250/0.500IN | | | | | | | | | | | |
| 90 | 48.0 | 150.2 | | SEAMLESS START | | | | | 69 | 45 | 55.12 | 33 | 27 | 21.33 | 522.3 |
| 90 | 0.0 | 150.2 | | NWT 0.500/0.250IN | | | | | | | | | | | |
| 100 | 13.8 | 164.0 | | SEAMLESS END | | | | | 69 | 45 | 54.00 | 33 | 27 | 22.77 | 523.4 |
| 100 | 0.0 | 164.0 | | | | | | | | | | | | | |
| 110 | 23.5 | 187.5 | | BEND-COLD LEFT | | | | | 69 | 45 | 53.88 | 33 | 27 | 22.79 | 523.4 |
| 110 | 13.1 | 200.6 | | | | | | | | | | | | | |
| 120 | 34.7 | 222.2 | | | | | | | 69 | 45 | 53.12 | 33 | 27 | 23.44 | 523.5 |
| 130 | 34.8 | 257.0 | | | | | | | 69 | 45 | 53.10 | 33 | 27 | 24.12 | 523.6 |
| 140 | 33.7 | 290.7 | | | | | | | 69 | 45 | 52.09 | 33 | 27 | 25.12 | 523.6 |
| 150 | 47.6 | 338.3 | | | | | | | 69 | 45 | 52.00 | 33 | 27 | 26.94 | 524.1 |
| 150 | 9.9 | 348.2 | | BEND-COLD OVER | | | | | | | | | | | |

METHOD AND APPARATUS FOR DETERMINING LOCATION OF CHARACTERISTICS OF A PIPELINE

CROSS-REFERENCE TO RELATED APPLICATIONS

None.

STATEMENT REGARDING FEDERALLY SPONSORED RESEARCH

None.

BACKGROUND OF THE INVENTION

1. Field of the Invention

The present invention relates to a multi-parameter pipeline measurement device, and more specifically to integrated pipeline defect and anomaly detection, pipeline mapping, and identification of defect/anomaly location.

2. Description of the Related Prior Art

Underground pipelines are widely used in a variety of industries, allowing a large amount of material to be transported from one place to another without disrupting other activity on the surface of the land under which the pipelines run. A variety of fluids, such as oil and/or gas, as well as particulate, and other small solids suspended in fluids, are transported cheaply and efficiently using underground pipelines. Subterranean and submarine pipelines typically carry enormous quantities of oil and gas products indispensable to energy-related industries, often under tremendous pressure and at high temperature and at high flow rates.

Unfortunately, even buried pipelines are not completely protected from the elements. Corrosion of a pipeline can cause small spots of weakness, which if not detected and fixed, could result in a pipeline catastrophe. Subsidence of the soil, local construction projects, seismic activity, weather, and simply wear and tear caused by normal use can lead to defects and anomalies in the pipeline. Also, harsh environments can cause pipelines to move gradually over time, thus making location of the pipeline difficult. Shifts in the pipeline location can also lead to defects, cracks, leaks, bumps, and other anomalies, within the interior of the pipeline.

Defects and anomalies can appear in the surface of the pipeline. Both the internal and external surface of the pipeline can be damaged by environmental factors such as the reactivity of the material flowing through the pipeline, the pressure, temperature and chemical characteristics of various products and contaminants inside and outside the pipeline, corrosion, mechanical damage, fatigue, crack, stress, corrosion cracks, hydrogen induced cracks, distortion due to dents or wrinkles, exposure, and damage to weight coating and free spanning of offshore pipelines. Moreover, submarine pipelines face a hostile environment of ships anchors, troll boards and seabed scouring due to strong currents. Although timely repair or maintenance of pipelines can lengthen the service lifetime of the pipeline, a rupture or serious leak within the pipeline can be difficult and expensive to repair and can be difficult to locate.

PRIOR ART PIPELINE INSPECTION

The resulting cost to industry as well as the potential for damages to human life can be great, as the efficiency of using the pipeline is adversely affected by the anomalies. Consequently, industry has produced various inspection devices for detecting defects and anomalies. For example, U.S. Pat. No. 4,285,242, issued Aug. 25, 1981 and assigned to British Gas Corporation, of London, England, teaches a pipeline inspection apparatus that includes a vehicle capable of moving along the interior of the pipe by the flow of fluid through the pipe to inspect the pipe for location of anomalies.

Such prior inspection vehicles or pigs have also typically included wheels, spring loaded to be urged against the interior of the pipe, and have further included odometers that count the number of rotations of the wheels. Ultrasound receivers have been located within the wheels on an inspection vehicle themselves. Various measurements have been made by the wheels, which have included the ultrasound receivers, the odometer, and calipers that measure the position of the wheels relative to the body of the vehicle as the wheels encounter various curvatures of the pipe in order to allow the inspection vehicle to map the pipeline. The inspection vehicle has been used to record shape of the pipeline according to the ultrasonic signature received by ultrasonic transducers located within the wheels of the inspection vehicle, each data sample associated with an odometer measure.

Other related technologies have included measurement devices such as ultrasonic transducers mounted on an inspection unit within the pig which emit high frequency sound and measure and record the reflected and refracted signals from the walls of the pipe. Such measurement devices have typically been used to examine the interior of the pipe.

Test personnel have loaded pigs into pipelines recorded various signals from emitted magnetic fields, recorded the data within the pig, and then examined the data after completion of the run, extracting also defect and anomaly signatures, as well as the location of such anomalies.

Unfortunately, repairing a detected defect can be a monumental undertaking. Repair teams, equipped with detailed maps showing the location of the buried pipeline beneath the ground from previous surveys, have placed pegs in the ground immediately over the pipeline where shown on the maps. Using the information obtained from the inspection vehicle, repair teams have been able to "walk the pipeline," following along the pegs to a distance corresponding to an odometer measured distance digging down to the pipeline and then visually identifying and mechanically repairing the pipe.

Minor variations, such as vehicles having multiple interconnected portions, a first portion propelled along the interior of the pipe by the fluid moving through the pipe and a second portion containing the inspection apparatus, are also known and widely used. Such inspection vehicles may be somewhat more flexible, and may report interior characteristics of the pipe with somewhat greater accuracy.

PRIOR ART MAPPING

Not only is the identification of defects and anomalies crucial to pipeline maintenance, but the location of the pipeline itself can be problematic. Many of the environmental stresses on the pipeline that cause defects and anomalies to appear in the pipeline can also shift the pipeline location. This is particularly true of very long pipelines.

Locating or mapping the pipeline has typically been accomplished by inserting a pipeline pig within a pipeline to inspect the interior of the pipeline for the locations of the pipeline, that is, its curvature or profile. For example, U.S. Pat. No. 4,747,317 to Lara, issued May 31, 1988 teaches a pipe survey pig including an onboard inertial reference unit and signal processing units for receiving acceleration and angular velocity signals generated by the inertial reference unit calculating resultant values of angular velocity in accelerations and averaging the calculated result to provide recordable signals related to the position of the pig and curvature of the pipe.

Also, U.S. Pat. No. 4,717,875, also issued to Lara, Jan. 5, 1988, teaches measuring the change in curvature or displacement of a section of submarine of subterranean fluid transmission pipeline. Lara '875 teaches traversing the pipeline with a pig have in onboard instrument package including accelerometers and a longitudinal positioning measuring device comprising a magnetonometer for counting the girth welds or other known magnetic anomalies along the section of pipeline to be measured. The magnetometer is carried by the pig, and determines distance traveled by counting welds of a known distance apart. These systems for measuring the curvature or displacement of the pipeline have allowed mapping of subterranean and submarine pipelines to a generally adequate level of precision.

PRIOR ART USES OF AN IMU TO MAP

The concept of using inertial technology in the pipeline surveying application was recognized in the 1978 time frame where it was identified as an example of "land surveying". Many examples of land surveying (or "land navigation") subsequently appeared in the literature which used inertial measurements in combination with odometry and zero-velocity updates available at enforced stops. It is known to use initial guidance technology within a pipeline pig, in conjunction with, post-run software using error minimizing techniques such is Kalman filters, to determine pipeline location or curvature direction or profile, and ovality.

Mapping of pipelines by the use of inertial sensors has been a practice in the pipeline industry for several years. Separately, pipeline inspection has been used to locate defects and anomalies in pipelines. However, neither process, by itself, adequately provides a complete picture of the pipeline, sufficient for a repair team to find and repair a defect. Purely inertial and internal inspection devices cannot compensate for the background drift of the pipeline location, since internal inspection apparatuses record defect location according to contemporaneous odometer measurements. Conversely, inertia systems used for mapping the drift in the pipeline location have not been used for pipeline inspection.

Moreover, with respect to the pig's location very little attention has been paid to error sources within the inertial measurement unit and odometer. While errors may be neglected when a very short pipeline is used, longer pipelines imply a sufficient distance and run time to allow errors to accumulate. Errors within the odometer caused both by the wear and tear on the rim of the wheel through repeated uses of the inspection vehicle and also caused by slippage between the wheel and the surface of the pipe has lead to errors in the distance to anomaly resultant calculations. Ultrasonic data can be corrupted by vibrations and turbulence within the pipeline as well as by activity external to the pipeline. Moreover, having only a small number of error detection mechanisms within the pipeline inspection vehicle traveling through the pipe, has led to accumulated errors in location. Consequently, repair teams have dug in several places attempting to locate the pipeline anomaly as reported by the inspection vehicle.

U.S. Pat. No. 4,995,775 discloses a pipeline monitoring system using strapdown inertial guidance system and redundant sensors to measure one or more dynamic characteristics, and offsite processing software to compare such dynamic signals or provide resultant pipeline profile information.

SUMMARY OF THE INVENTION

Briefly, the present invention includes a large number of sensors, some of which are located on the inspection vehicle, and others of which are located on or under the surface of the ground adjacent to the pipeline. The system also includes a subsystem for inspecting the pipeline and for reporting the location of defects and anomalies in the pipeline. The system also includes a subsystem for compensating for errors through Kalman filtering. The system also includes a subsystem for reporting defect location according to a global positioning system (GPS) in longitude, latitude, and altitude (depth).

More specifically, the present invention includes magloggers, also known as "loggers," which are sophisticated devices located along the pipeline which provide data used in the post-processing routines. Magloggers are placed along the pipeline, laid along the surface of the ground as close to the pipeline as practicable, before the pig is inserted into the pipeline. Maglogger location is known accurately by the use of a differential global positioning satellite technique described below, as is known in the art, and the maglogger data is optimally correlated to data from the inspection vehicle to provide exceptionally accurate information. The logger positions are established using differential GPS, so the position of each logger relative to all others is accurately known to within a few centimeters.

The magloggers each contain a highly precise clock that is synchronized to a similar clock within the pig before the pig is placed within the pipeline. Also, the magloggers each contain a fluxgate magnetometer and a recording device for detecting and recording the precise moment the pig passes. Once placed in position, the magloggers enter a "sleep" mode in which the magloggers use very little energy. Subsequently, the magloggers detect the approach of the pig along the pipeline, transition from the sleep state to a full-power state, and detect the passage of the vehicle by measuring the magnetic signature of the inspection vehicle passing through the pipeline. The exact time the pig passes is stored within the maglogger, and each data value is separately time tagged, stored by the maglogger using its own unique data storage means. The output of each logger is an envelope of data representing the magnetic signature of the pig as the pig passes the logger, from which the precise time of the passage of the pig may be determined.

The improved pig of the present invention contains magnetic sensors for inspecting the whole of the pipeline, both the external and the internal structure of the pipeline. The magnetic sensors include metallic brushes that are maintained in contact with the internal surface of the pipeline despite changes in the pipeline diameter and despite radial movement of the pig within the pipeline cross sectional area by resilient members that urge the brushes against the surface of the pipeline. The magnetic sensors allow the pig to identify the detection of structural defects and anomalies within the pipeline as discrete events.

The improved pipeline pig also has an inertial measurement unit having both gyroscopic and accelerometer sensors, an improved odometer for measuring the distance traveled by the inspection vehicle, and if desired sensors measuring the location of the wheels relative to the body of the inspection vehicle itself, which detects areas where the pipeline narrows as the wheels are pressed toward the body of the inspection vehicle. The odometer measurements include the incremental angular displacements of each odometer wheel, and a "fastest of three" means for selecting from among the various wheels of the odometer of the at each interval of time.

The pipeline pig of this invention also includes a precise clock that records the time of a detection of an anomaly or defect, according to a precise clock located within the inspection vehicle itself Consequently, the detection of defects and anomalies by the inspection vehicle can be translated to location not only in terms of an odometer measure, but also in terms of the distance to each maglogger. The clock allows the odometer data to be time stamped, while the odometer sampled and stored at a nominal 50-Hz rate. Typically, three odometer wheel outputs are available, and these are from wheels spaced 120 degrees apart around the circumference of the pig.

It will be readily apparent from a review of this disclosure that the pig can generate an enormous amount of data, since the measurements of several sensors are recorded at a moderate data rate over a long pipeline distance. Thus the present pig includes both inertial subsystems and pipeline inspection subsystems within the same overall pig. The gyroscope and accelerometer sensors within the inertial measurement unit, in combination with the odometer and the loggers, provide pipeline location information. Also, within the same overall system, a pipeline inspection apparatus within the pig detects defects and anomalies, on both the internal surface and the external surface of the pipeline. Moreover, both the mapping subsystem and the defect/anomaly detection subsystem provide data files indexed by a highly precise clock within the pig.

The problem of interest is defined in general to be one where the 3-dimensional position (along-track, cross-track, vertical) of a pig is to be accurately determined as a function of elapsed time in a pipeline surveying application. During the field test operation, data is collected from various subsystems and stored in real time. However, the data are analyzed off-line, in a set of post processing routines executed in an off-site computer system.

Also, simultaneously during the pipeline survey, a set of outputs from an array of magnetic sensors are sampled and stored at a high rate and time tagged using the pig on-board clock. This data is time correlated to the pig position data as a means of defining the positions of pipeline features and defects, such as corrosion anomalies.

The scenario normally applicable in the pipeline inspection application is as follows. The pig is inserted into the pipeline though a trap specifically designed for this purpose, and then released. After a predetermined delay the pig is powered up, at which time the data collection and storage processes begins. The desired operation of the pig of this invention avoids a make-ready phase in which the pig is powered up and held stationary outside the pipeline for the purpose of initialization. This means that, at the time of power-up, the initial position, velocity, and attitude of the pig are generally unknown, or only approximately known. A logger spacing of 5 km is desired for cost-effective pipeline surveying. A 1-sigma accuracy of 1.0 meters at 2 km of travel is desired for locating pipeline features and faults.

The data collected in real-time by the various devices described above is post-processed to yield a result with the highest accuracy possible in defining the 3-dimensional position of pipeline features and faults in GPS coordinates. This is accomplished using a self-initializing set of strap-down attitude reference/navigation algorithms, a set of dead-reckoning algorithms, and a set of optimal filtering and smoothing algorithms.

To address this problem, the present invention further includes an off-site post processing station that includes a computer system for running error correction and compensation routines based upon Kalman filtering. The error detection and correction routines, however, are run after the field run is completed. Data are downloaded from the magloggers and the pig into the computer system, and the data files stored in each is copied into RAM of the off-site computer system. The off-site computer system receives data files from the pig and from the magloggers after a field test is run, and by using additional data obtained from the magloggers, actually generates a set of error corrections based upon the data files recorded within the pig and then uses the error corrections to improve results of the field test.

The post-processing computer system calculates an inertial navigation solution consisting of an attitude matrix, a velocity vector, for each clock interval of the field run. The computer system then executes an optimal filter, determining a set of error corrections based upon the known maglogger locations and the measured pig locations. The error corrections include calculations of the boresight errors, odometer scale factor and other errors. The entire data set measured from the pig is then rewound and recomputed, with the error corrections subtracted therefrom.

According to the present invention, the use of odometer data to aid the inertial navigation solution takes a unique form consisting of the arc length of the pig travel integrated over the update interval. This is in contradistinction to conventional usage in which the odometer-derived aiding signal is used to provide a measure of speed. Also, according to the present invention, the periodic logger position fix-data may be used either as a supplement to the odometer arc-length measurement, or in lieu of it to aid the inertial navigation solution. Further, according to the present invention, the pig position at all interior points between each set of reference points may be refined using optimal smoothing, which is a natural complement to the optimal filtering process that is used in directly aiding the inertia navigation solution.

The post-processing software routines of the present invention also include a sophisticated set of software processes for analyzing the data reported by the various sensors within the inspection vehicle and the data reported by the loggers. By utilizing such post-inspection routines, errors are removed and improved information is provided. Moreover, because the location of the logger is known in terrestrial coordinates such as longitude, latitude, and altitude, or other similar land measure, the location of the defects can be reported in such coordinates to avoid the need to "walk the pipeline". The software processes, however, go a step further, and allow repair teams to use differential Global Positioning Satellite Signals ("GPS") to locate defects with a very high degree of accuracy and precision. As will be recognized in reading the Detailed Description, a repair team having a first GPS sensor at known location can use signals received from the Global Positioning Satellites operated by the United States military to locate any point on the earth with great accuracy. Consequently, the processes, by reporting the location of defects in a global position satellite reference frame, allow the repair team to know precisely where to dig to find a defect reported by the present inspection vehicle and loggers of the present invention.

The approach utilized in the pipeline inspection vehicle of this invention represents a unique application of: inertial navigation technology; in combination with accurate Global Positioning System (GPS) position information; in combination with precision odometry; in combination with optimal filtering and smoothing techniques. These elements are all combined in a unique manner to achieve highly accurate position a pipeline network at all points along its length.

BRIEF DESCRIPTION OF THE DRAWINGS

FIG. 9 is a chart presenting an exemplary output file of the post processing routines.

DETAILED DESCRIPTION OF INVENTION

The preferred embodiment of the invention of a pipe inspection pig and signal process system, includes both hardware implementation and information processing, as described in the following paragraphs.

1.0 THE PIPELINE INSPECTION AND REPORTING SYSTEM

Figure 1:
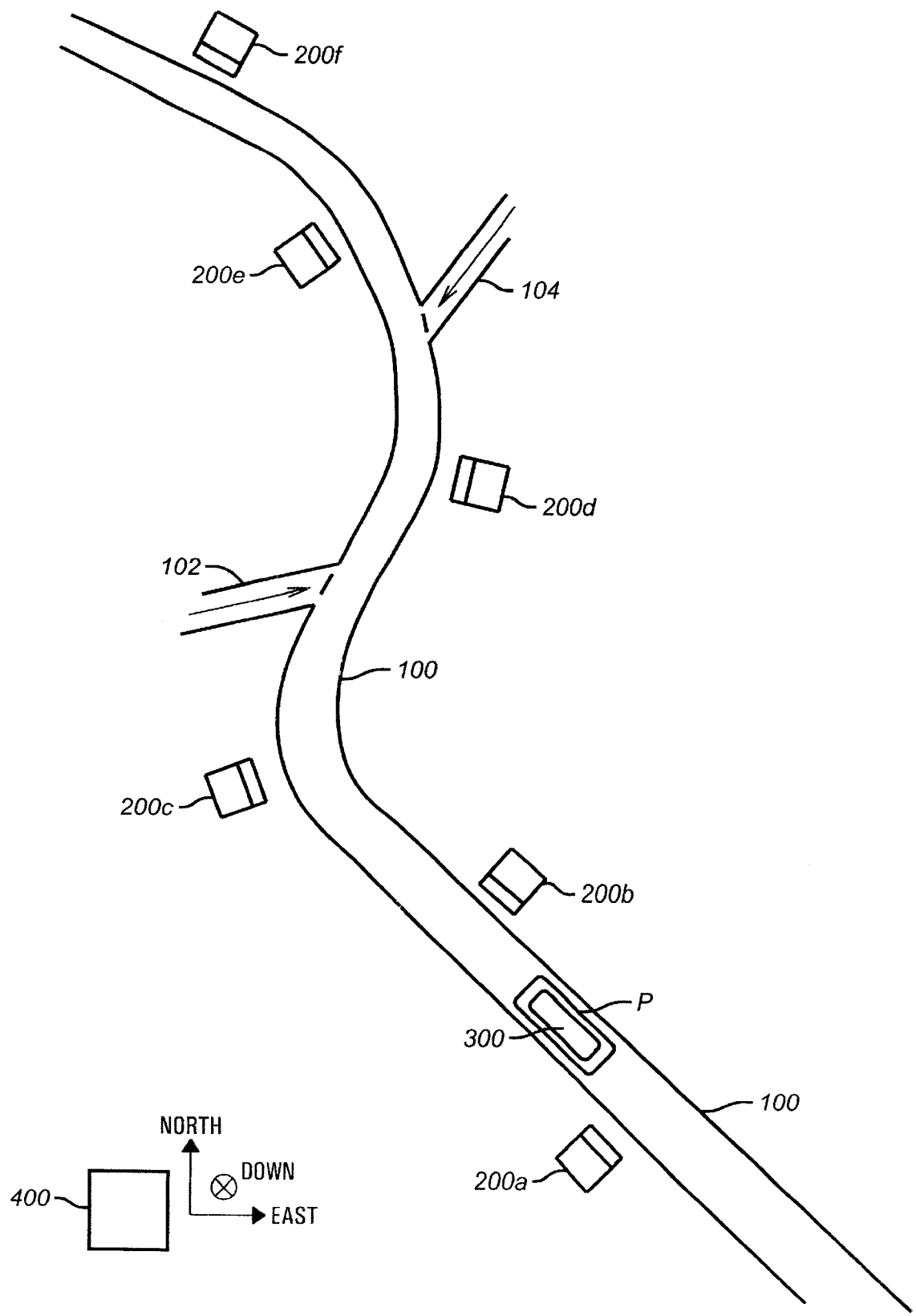
FIG. 1 is a schematic view of the pipeline inspection and reporting system of this invention mounted in a pipeline.

Referring now FIG. 1 a generalized pipeline pig field assembly system P is shown. A typical pipeline 100 is buried beneath the surface of the earth to a depth of at least several feet. The location of the pipeline 100 has typically been recorded by surveyors such that the pipeline can be located. The pipeline 100 is long, measuring at least several hundred kilometers in length. The pipeline 100 also has various curves, as the path of the pipeline circumvents structures, such as buildings, plants, and subterranean rock formations.

The pipeline 100 is connected to incoming pipelines or piping for receiving the flow of fluid, such as oil and/or gas. Pipeline 100 also has several off-take paths such as 104 for diverting a portion of the fluid flowing though the pipeline to an another pipeline. A hydrocarbon gas such as natural gas flows through the pipeline, the hydrocarbon gas is pressurized pipeline at a plant, which may be a drilling platform or a processing facility, or other structure.

Figure 2:
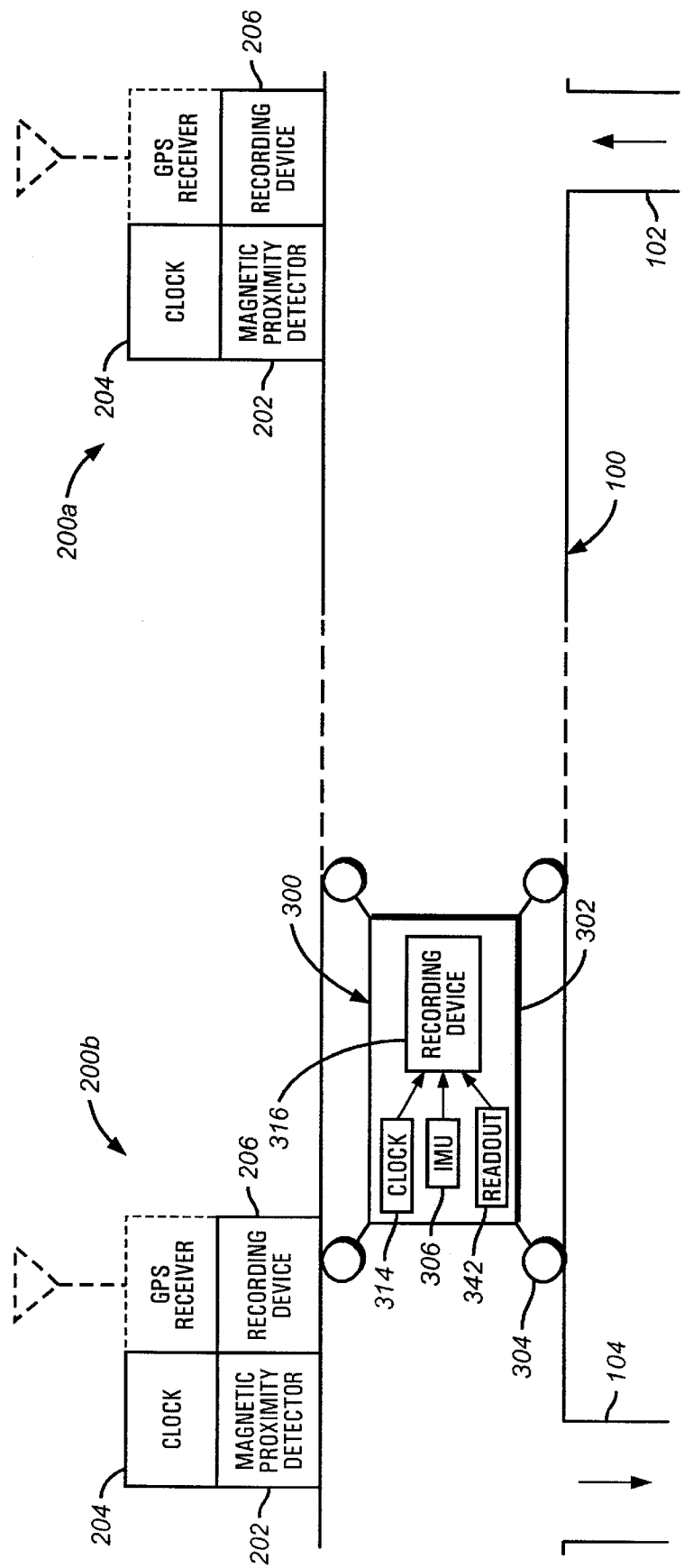
FIG. 2 is a schematic view of the pipeline line inspection pig in conjunction with magloggers located at fixed positions outside the pipeline.

Also shown in FIG. 1, several magloggers 200a–200f are located along the path of the pipeline. The magloggers, described in further detail with reference to FIG. 2, are located at known positions on the surface of the ground adjacent to the pipeline P, or are buried beneath the ground adjacent to the pipeline 100. The magloggers 200a–200f are oriented in a direction appropriate to the location of the pipeline 100, as described in greater detail with reference to FIGS. 5A–5B.

Also shown in FIG. 1, a pig 300 containing an inspection apparatus is mounted with the pipeline 100. The inspection apparatus, described in greater detail with reference to FIG. 4, allows various measurements to be taken from within the pipeline 100. Because the inspection apparatus is located within the pig 300, components of the inspection apparatus are hereinafter described as components of the pig 300.

Also shown in FIG. 1, a portable computer 106 and a GPS receiver 108 may be carried to the location of each maglogger 200a–200f in turn. At each maglogger location, the GPS receiver 108 allows the portable computer 106 to create a data file containing maglogger locations in GPS coordinates, i.e. terrestrial coordinates of North, East and down (or latitude, longitude, and depth). If desired, the GPS receiver 108 may be located within each maglogger itself, or the GPS data may be stored within each maglogger. As will be explained below, the present invention contemplates differential GPS surveying using data obtained from a roving GPS receiver 108.

Also shown in FIG. 1, an off-site computer system 400 at an off-site station allows subsequent data processing of various measurements. These measurements include data recorded by a recorder 316 of the inspection apparatus 302, described in reference to FIG. 3, and by each of the magloggers 200a–200f described in reference to FIGS. 5A and 5B. The off-site computer system 400, as well as various processing methods and procedures executed thereon are described in greater detail with reference to FIGS. 6, 7 and 8.

Referring now to FIG. 2, a schematic drawing of the hardware elements utilized in the pipeline surveying system P, which consist of both on-board and off-board elements, is shown. The on-board elements mounted with the pig 300 consist of an inertial measuring unit, an odometer assembly and associated readout, a clock and a recording device that allows data from each of the subsystems to be recorded during the survey. The off-board elements of the magloggers such as 200a consist of a magnetic proximity detector, a clock synchronized to the pig on-board clock, and a recording device that allows the pig time of passage to be recorded.

Referring now to FIG. 2, a schematic representation of the pipeline pig assembly is shown in greater detail. FIG. 2 shows a pig 300 having an inspection apparatus and various magloggers 200a and 200b along the pipeline 100. As will be explained below, farther in reference to FIG. 3, the pig 300 includes an IMU 306, a clock 314, a recorder 316 (also referenced to as a recording device), and an odometer apparatus 304 having a readout 342. Also, as further explained below in reference to FIGS. 5A and 5B, each of the magloggers 200a and 200b includes a magnetic proximity detector 202, a clock 204, and a recording device 206. Each maglogger 200a and 200b further includes a means for connecting to a GPS receiver 212, either directly or via a portable computer system. The GPS receiver 212 may, if desired, be included within each maglogger. The GPS reciever 212 receives signals from global positioning satellites maintained by the United States Defense Department As further shown in FIG. 2, the pipeline 100 has an intake channel 102 and an out take channel 104. The intake channel 102 receives additional fluid into the pipeline 100, and additional fluid into the pipeline 100, and may be regarded as the convergence of two or more pipelines. The offtake channel 104 allows fluid to flow out of the pipeline 100 and may be regarded as the divergence of the pipeline 100. Intake channels 102 and outtake channels 104 often inject a lateral thrust to a pig 300 moving along the pipeline 100.

1.1 THE PIPELINE PIG AND OFF-SITE PROCESS STATION—GENERAL COMPONENTS

Figure 3:
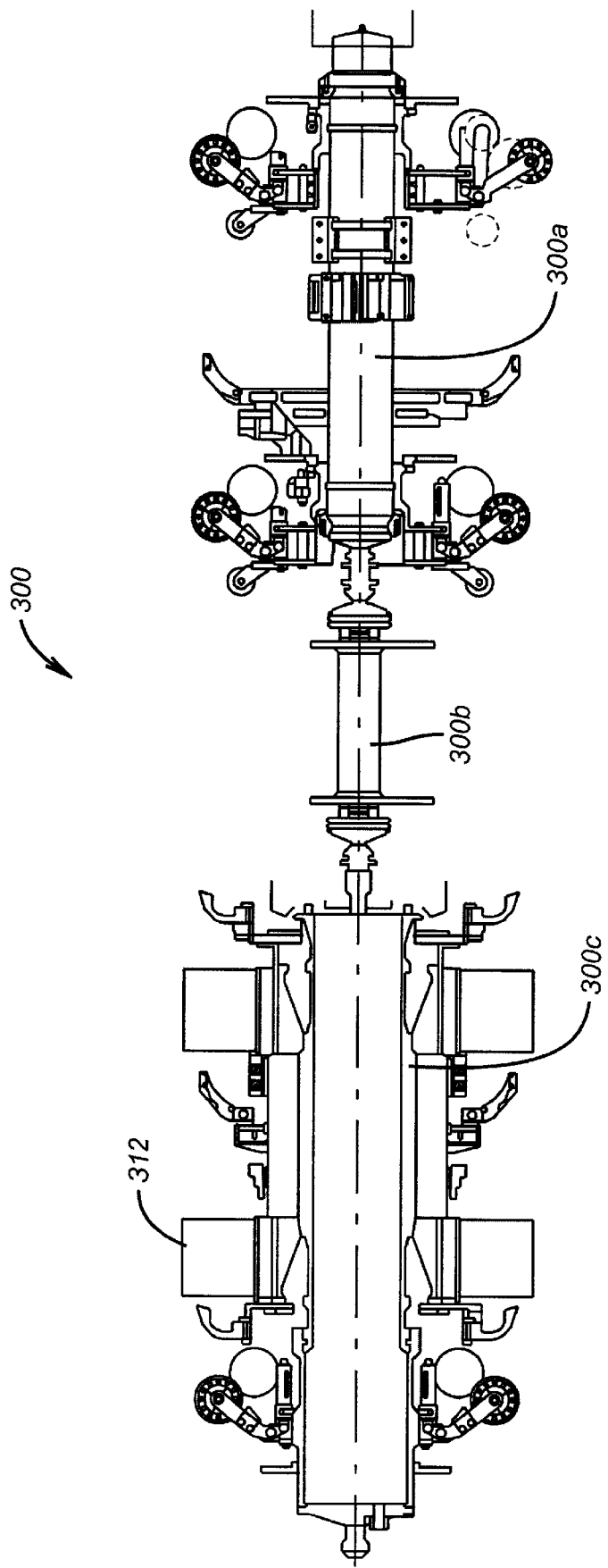
FIG. 3 is an over-all assembly drawings of the pipeline inspection and reporting vehicle.

Referring now to FIGS. 2 and 3, the inspection apparatus of the pig 300 is shown in greater detail. It will be remembered that the pig 300 contains several components for several different functions relating to pipeline inspection. It will also be remembered that the overall system P of FIG. 1 includes not only the pig 300, but also the magloggers 200*a*–200*f* and the off-site process station 400.

As shown in FIG. 2, the pig 300 contains several components within the inspection apparatus. The pig 300 contains an odometer assembly 304 for measuring the overall distance traveled by the pig 300 through the pipeline 100, inertial sensors within an inertial measurement unit (IMU) 306 having gyros and accelerometers, and a pipeline inspection device 312 (FIGS. 2 and 3). The inertial measurement unit (IMU) 306 is for measuring the orientation and acceleration factors of the pig 300. The pig 300 also includes a clock 314, which provides accurate time to be used in the subsequent data processing phase as the means of synchronizing all of the on-board and off-board measurements. Finally, the pig 300 includes a recording device 316 that allows the IMU, odometer, and clock outputs to be recorded at a rate sufficient for the needs of the subsequent data processing phase.

Each of the more significant components of the pig 300 is now described in detail.

1.3.1 INERTIAL MEASUREMENT UNIT (IMU)

Referring again to FIGS. 2 and 3, the inertial measurement unit (IMU) is a strap-down sensor that measures kinematic properties of the pig. The strap-down inertial measurement unit 306 consists of an orthogonal triad of gyros, an orthogonal triad of accelerometers, and a digital processor that compensates the sensor outputs, and converts them into a form suitable for storage. The gyros measure the change and orientation of the inspection vehicle with respect to inertial space as the pig 300 housing inspection component 302 changes in orientation, for example as the pig 300 passes around a bend in the pipeline 100, register the change relative to inertial space. Consequently, the angle between the gyros and the centerline of the inspection vehicle 302 increases or decreases as the orientation of the inspection vehicle changes.

The inertial measurement unit (IMU) is a strap-down sensor that measures kinematic properties of the pig. The inertial measurement unit is mounted with the defect sensor on the pig, and consequently defines a "pig-originated" coordinate system, defined by the instantaneous location and orientation of the pig. The data generated by the inertial measurement unit includes the readings of the accelerometers and gyroscopes, and are such as may be used for measuring the relationship between the pig-originated coordinate frame and an inertial frame.

Accelerations can be the result of centrifugal force as the inspection vehicle rounds a corner, the lateral thrust of additional fluid material as the inspection vehicle passes an intake 102 or offtake 104 (FIGS. 1 and 2) turbulence in the pipeline, or other causes. In the preferred embodiment of this invention, the IMU 306 is manufactured by Honeywell, Inc.; ModelHG1138, although other IMU's are also contemplated.

As will be appreciated by those skilled in the art upon reference to this description, errors can enter inertial measurement sensors such as the gyros and accelerometers. Such errors tend to accumulate, causing minor deviations between true inertial rotation and rectilinear acceleration and the measured quantities.

1.3.2 THE DEFECT/ANOMALY INSPECTION SYSTEM

The pig also carries a defect/anomaly inspection unit that generates defect/anomaly inspection data describing both the location and the nature of the various defects in the pipeline that are encountered. The defect/anomaly inspection unit has a magnetic sensor for detecting and evaluating defects and anomalies of the pipeline. If desired, the magnetic sensor may be replaced with other types of defect/anomaly inspection units, such as accoustical sensors.

Referring again to FIG. 2, the pig 300 further includes a magnetic sensor within a defect anomaly inspection system 312, for detecting magnetic defects within the pipeline surface itself. As will be recalled upon review of United Kingdom Patent No. 1,532,242 and 2,086,051, assigned to British Gas, the detection of magnetic characteristics of a pipeline using a magnetic flux leakage technique is well known in the art. Such a component is included within the pig 300 for detecting the magnetic flux leakage of the pipeline.

The magnetic sensor within the defect anomaly inspection system 312 contains a cylindrical mild steel body, having on each end an annular arrangement of high strength permanent magnets. The permanents are magnetized radially so as to give a north pole on the outer of one magnet ring and a south pole on the other. The magnetizing unit also includes an annular arrangement of radial mild steel bristles, coupling the flux from the permanent magnets to the inner pipe wall. The bristle assembly also assists in providing suspension, and maintaining the unit centrally in the pipe. The magnetizing until thus magnetizes the pipe wall axially, as it travels down the pipeline.

The magnetizing unit also includes an array of sensors in the form of a ring positioned between the magnetic poles of the unit which map the flux density at the internal surface of the pipeline and detect any defects or anomalies which may be present. The Magnetic sensor allows detecting and sizing the metal lost defects. As shown in FIG. 3, the sensor 312 is or the vehicle between the two pole pieces, at an angle of 45 degrees on a hinge that flattens out. The sensor is mounted on a flattened out portion at the extreme end of the sensor ring. Flexible bristle arrangements obtain the field level into the pipe wall. Immediately beneath the bristles are magnets which are mounted around the body of the vehicle. The whole unit is referred to as a MTV, or magnetic tractor vehicle, and is a magnetizing unit as a whole. The magnetic circuit runs down through the bristles, along the length of the vehicle, through a return path and back out through the other magnetic and pull pieces so there is a cylinder underneath the magnetic with a ring of magnetic running around the outside, with bristles on top.

For further background on the inspection system 312, please refer to British Patent No. 1,535,252 issued to British Gas Corporation and British Patent No. 2,086,051 also issued to British Gas Corporation.

1.3.3 ODOMETER ASSEMBLY

The pig's kinematic sensor also has an odometer apparatus for detecting the overall, curvolinear distance traveled by the pig. The odometer apparatus, like the inertial measurement unit, is mounted within the pig.

Referring again to FIG. 2, the odometer assembly 304 is provided for measuring overall distance traveled by the pig through the pipeline 100. The odometer assembly 304 comprises a precisely machined set of three wheels at 120 degree separations relative to each other around the circumference of the pig 300, pivotally spring mounted at each end of the pig 300. The wheels of the odometer 304 are urged toward the interior walls of the pipeline 100 by springs or other resilient mechanism. Consequently, the wheels of the inspection apparatus roll along the interior of the pipeline 100 as the pig 300 is carried through the pipeline 100 by the fluid. It will be remembered that the fluid may be liquid or gas, and may have solid particles in suspension. Because the circumference of the wheel is known, counting the number of rotations made by the wheel as it is carried along the pipeline 100 allows the on-board microprocessors 318 to provide an estimate of the overall pipeline length.

Each of the wheels has a metallic device mounted on the wheel that has a fine-pitch set of gear-teeth or points of the star, also known as castillations, around the circumference of the wheel. The castillations are placed on one of the surfaces of each the wheel, spaced substantially equadistantly from one another around the the wheel. The castillations may be shaped as "Fingers" pointing from the center of the wheel outward toward the edge of the wheel.

The odometer apparatus also includes a variable-reluctance transducer mounted on the body or chassis of the pig adjacent to each wheel. The transducer senses the passage of one of the castellations and generates a queuing pulse signal in response thereto. When the wheel is orientated with any of the castillations immediately adjacent to the transducer, the wheel causes the odometer to assert the signal. When the wheel is orientated with none of the castillations immediately adjacent to the transducer, the wheel causes the odometer to deassert the signal. It will be recognized that this arrangement has an additional benefit that the assertion of the signal is substantially dependent on the distance traveled relative to the pipeline and substantially independent of pig speed relative to the pipeline. Because a large number of castellations are mounted on each wheel and the passage of each past the transducer causes the transducer to generate the signal, the odometer apparatus generates a large number of signals as the pig moves along the pipeline.

As will be explained below in reference to the post processing operations and more specifically in reference to FIG. 8 various errors enter the odometer measurements. For example, simple wear and tear on the edge of the wheels shown in FIG. 2 gradually reduces the overall radius and circumference of the wheels. Also, slippage between the wheels and the pipeline interior adds further error to the odometer measurements. These errors are compensated in the post processing methods of the present invention described below. The gradual wear and tear on the odometer wheel produces a scale factor error, which is a multiplicative value of each of the wheels. Also, the slippage may be modeled as a statistic process which may be modeled as a guassian noise.

To minimize the effects of one of the wheels sticking or slipping against the inner surface of the pipeline 100, the odometer apparatus uses a "fastest of three" approach to reducing the effects of wheel slippage or sticking. According to this approach, only the wheel that has rotated by the greatest angle over the most recent time interval is used during that time interval. When any of the wheels has rotated by this incremental amount, the odometer apparatus generates a queuing signal to a scan assembler (described in reference to FIG. 4) within the pig's on-board data acquisition system. The on-board data acquisition system responds by creating a data record, containing instantaneous readings of various on-board sensors.

It will be recognized upon reference to this description that the relegation of queuing signal generation to the odometer apparatus 304, rather than to the clock 314, allows the pig to create the queing signal substantially independently of velocity. The generation of the queuing signal in the present invention is distance dependent, rather than velocity dependent.

It should also be noted that the odometer is not used to measure velocity, and that no independent record is made of velocity over the given time interval. Rather, the odometer apparatus is used to measure distance traveled along the pipeline, and is used to generate queuing signals every 3.3 millimeters of circumference. Velocity may be used to support defect sizing functions, to monitor the product flow velocity provided by the pipeline operator during the inspection run, and as a means of monitoring the inspection vehicle mechanical performance. But odometer velocity is not used in post-processing routines. Also important velocity is not measured or calculated by the odometer. Moreover, velocity is not used redundantly with any other measure.

In addition, further enhancements to the accuracy of the odometer measurements may be achieved by accounting for the effect of wheel castoring on the measurement of distance traveled. This is accomplished using the inertial system to compute the castoring angle, which may then be used to adjust the readings obtained from each odometer wheel.

The odometer 304 also includes a pivot shaft, a rod end, a pin, a spring tube, an arm stop, a bump stop, a spring retainer, a bush silent bloc, a spring rod, a bush, various spacers, a scraper, an axle and various capacitors.

1.3.4 SUMMARY OF THE DATA ACQUISITION SYSTEM

Figure 4:
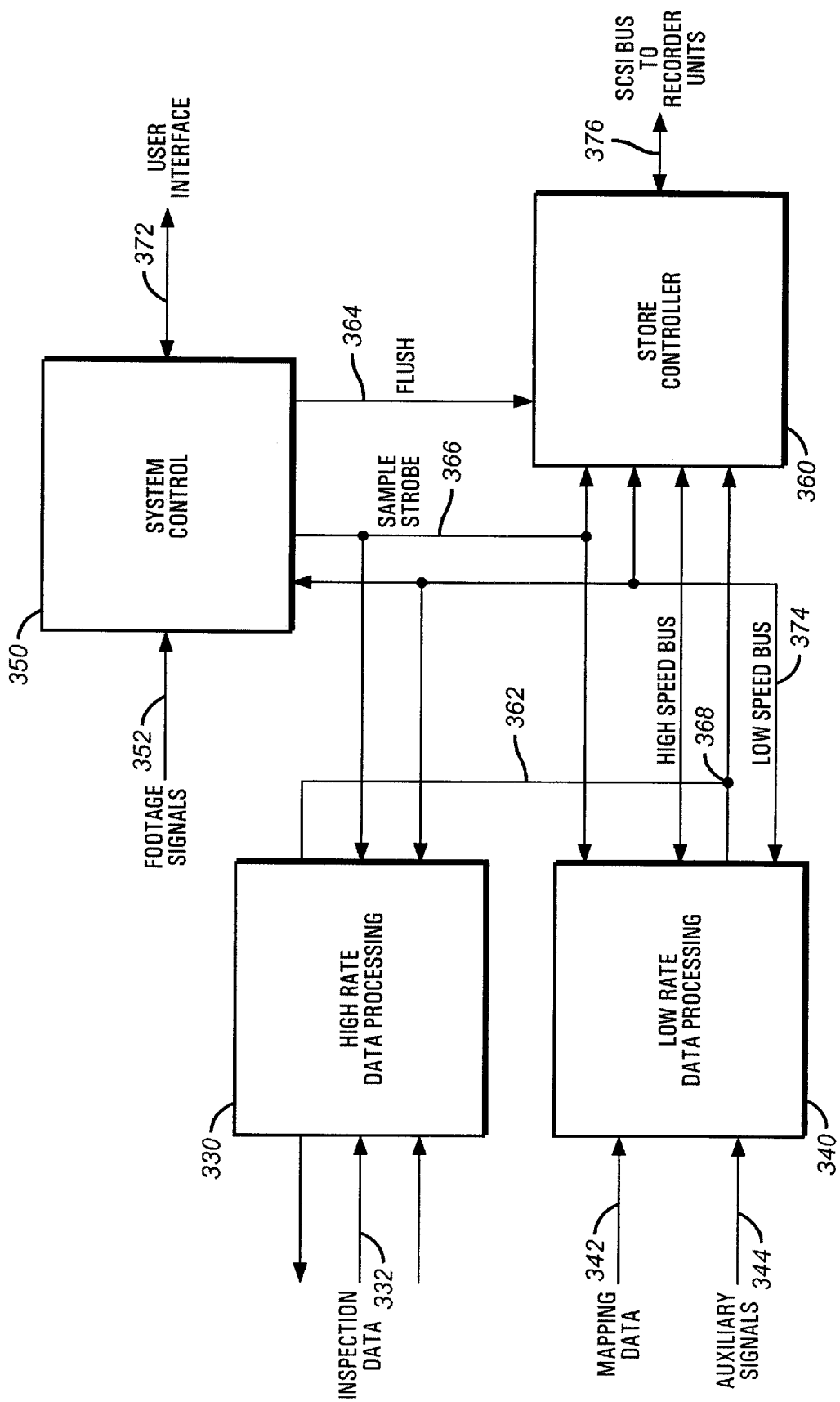
FIG. 4 is a flow chart of the Data Acquisition System.

Between the clock 314, IMU 306, odometer 304, and recording device 316, a data acquisition system including microprocessors comprises a data acquisition system. Referring now to FIG. 4, the data acquisition system within the pig 300 is shown. Inspection data 332 is obtained from the inspection device 312 at a high data rate. The inspection apparatus is therefore very sensitive; the high date rate, at any given flow rate through the pipeline 100 provides a high resolution. The processor 318 executes high rate data processing 330. In parallel, mapping data 342 and auxiliary signals 344 are received by the microprocessor 318 from the IMU 306, and are processed in a low rate data processing routine 340. The various data rates are provided by the various crystals of the on-board clock 314. As described above, the inspection device 312 provides detailed information about a variety of defects, including corrosion, cracks, and weld defects.

As will be apparent from review of FIG. 4, the various processes exchange data. The high rate data processing 330 and the low rate data processing 340 exchange data 362. The exchange of data 362 is not possible in prior art system that included only one subsystem. Moreover, the two processing routines 330 and 340 exchange data with a store controller 360 over a high speed bus.

Referring again to FIG. 4, footage signals 352 are received from the odometer apparatus 304. The footage signals 352 are provided to a system control routine 350. A Flush signal and a sample strobe 366 are included.

The high rate data processing 330 receives data from the main inspection sensors, including several hundred magnetic flux sensors, 312. The flux sensors indicate defects in the line, and are converted into digital signals and then processed by the functional block diagram high rate data processing 330 and are provided to a high speed bus 368. Every time the odometer apparatus 304 gives a new pulse the data is presented to the high speed bus 368, The low rate data processing 340 includes mapping and auxiliary signals, that take in all of the pigs environmental and positional data such as the time, distance, orientation of the pig in the pipe, the temperature and pressure. Although it is described as low rate data processing, the data from the low rate 340 processing system is presented on the high speed data bus 368. The data therein is combined together in a store controller 360. The store controller 360 includes a scan assembler, a data store, store controller, and a SCSI interface represented in that box described as store controller.

The scan assembler combines the records from the high rate data processing 330 and the low rate data processing 340 into a single record. Upon each odometer pulse, data from the defect sensors 312 and the auxiliary information are combined together in a single record. The records put sequentially in the record store, via the store controller. When there is enough data in the data store, the data store puts the data from the data store into the SCSI interface, from where the data is archived by the tape recorder. The tape recorder is a digital audio tape recorder.

The low speed bus that is shown from the system controller, 350 sets up the rest of the pig 300 at the beginning of the run i.e. if this acquisition pack is used throughout a range of sizes. This enables the system control to send the size and a number of other parameters to all the rest of the processing units. Then, during the run, the system controller 350 receives event messages from the other parts of the system and stores such messages in a non-volatile independent log which is examined at the end of the run. Because of the size of the pipeline, different gains are possible, because the pipe wall thickness can be different.

The low rate data bus 374 is set-up when it is in the pig trap, is pressurized, and the power is applied. The low rate data 374 bus is used to set-up the system, and to check that all parts of the system are working. It is a standard in engineering safety, to get the system up and running

A MICROPROCESSOR AND AN ANALOG-TO-DIGITAL CONVERTER

Referring again to FIGS. 2 and 3, also within the inspection apparatus of the pig 300 is a high-resolution analog-to-digital converter (ADC) which receives each signal from the gyros, accelerometers, and clock 314, and provides a high-resolution digital clocked value for each signal received. The pig 300 also contains microprocessors and other logic executing data acquisition programs during the duration of the battery power. The microprocessors perform a number of on-board real-time analysis functions, including the seletcion, formatting, buffering, and storing of data. Because the data sources provide real-time analog signals rather than digital signals ready for digital data storage, the ADC quantizes the data from the on-board measurement devices. The high-resolution digital value for each data source is provided to the on-board microprocessor that executes a software routine that reads the values and creates a data structure within the recorder 316. When initialized, the program causes the microprocessors to sample various on-board data sources at predetermined clock intervals, and to store the resulting data in an on-board recording device.

During the field run, during normal operation, the microprocessor 318 within the inspection vehicle creates a data structure within the recorder 316. The data structure contains measured values from the gyros, the accelerometers and the odometer apparatus 304 digitized by the analog-to-digital converter and clocked by clock, under the control of microprocessor 318.

The inertial measurement unit produces accelerometer data and gyro data; the odometer produces odometer data; when a defect is detected, the defect sensor produces defect data; and the clock produces elapsed-time data. Each of the data sources presents a signal representative of the corresponding property, and in conjunction with an on-board analog-to-digital converter, presents data to the on-board recording device in a format suitable for recording.

It will be recalled that the on-board data acquisition system is synchronized to the odometer wheel, rather than to the on-board clock. The odometer synchronization allows the resolution of the defect inspection device to be relatively constant even when the speed of the pig changes.

ON BOARD CLOCK

The pig also carries an on-board clock, measuring elapsed time. The on-board clock is snchronized to clocks within the magloggers 200a–200f before the pig 300 is inserted into the pipeline 100 (FIG. 1). As will be described with reference to the recorder 316, the on-board clock allows each data record to be time stamped as the record is created. Each data record within the on-board recording device contains contemporaneous information generated by on-board sensors. As will be further described in reference to the post-prociessing, time stamping of the data records allows each record to be associated within a substantially-simultaneous data record created by the magloggers.

Referring again to FIGS. 2 and 3, a clock 314 which provides accurate absolute time to be used in the subsequent data processing phase as the means of synchronizing all of the on-board and off-board measurements from an initial synchronization event. The clock within the pig contains a 16.00000 MHz crystal. The crystal is extremely precise, and has an extremely small drift with respect to time. The small drift ensures that time is accurately recorded even after a field run of several hours.

The on-board recording device adds a new data record to the on-board data structure whenever the odometer travels an additional 3.3 millimeters. It will be appreciated upon reference to the present description that the use of the odometer, rather than the clock, to queue the recording device allows the resolution of the data within the data structure to be substantially velocity-independent. In other words, as the pig speeds up or slows down within a the pipeline, the data rate of the pig according to the present invention increases or decreases accordingly, to provide substantially constant resolution.

As described above with reference to the odometer, each data record created within the recording device is time stamped. However, the data is not recorded in a clocked manner. Rather, the data is recorded whenever the odometer apparatus generates a queuing signal. The queuing signal is generated by the odometer apparatus whenever the fastest-rotating wheel describes a rotation of 3.3 millimeters of circumference. Consequently, although each data record is time stamped, the recording of the data record is performed when the odometer indicates that the pig has moved by a predetermined distance along the pipeline. The odometer-dependence allows for velocity-independence, in that the resolution of the various sensors is not reduced when the pig moves more quickly.

ON-BOARD RECORDER

The pig also carries an on-board recorder that creates various data records as the pig moves along the pipeline. The on-board recorder is preferably a digital-audio recorder (DAT), although other data storage devices such as a video recorder or flash-ROM may be used. The on-board recorder receives data records via the SCSI bus 376 when the data-store (within the store controller 360) is substantially full. Each such data record is already assembled by the scan assembler, which receives sensor data from the high-rate data processing 330 and the low rate data processing 340 via the bus 362.

Referring again to FIG. 4, the pig also includes a scan assembler that receives the clock signal, the odometer signal, the sensor data, and the inertial measurement unit, and assembles a data record containing the received data and signals. The data record is time stamped with a representation of the elapsed time received from the clock. The recording device stores the data record assembled by the scan assembler when triggered to do so by the queuing signal from the odometer apparatus. The time stamp is to at least $1/10$ second precision, or to greater precision.

Each data record includes the instantaneous readings of the accelerometers and gyroscopes, the instantaneous readings of the defect sensor, including the nature of the defect when a defect is detected, and a time-stamp. The time stamp is the instantaneous reading of the on-board clock. The various on-board data sources provide digitized, quantized data to an on-board scan assembler for time-stamping.

It will be appreciated that the use of a time stamp within the on-board data structure allows on-board data to be correlated in a post-process with data obtained from other devices that are not located within the pig, such as magloggers.

1.3.7 OTHER COMPONENTS OF THE PIG 300

Referring again to FIG. 3, the pig 300 includes, of course, a battery or other power source. In the described embodiment, the pig includes a battery fabricated on a printed circuit board mounted on a computer motherboard within the pig 300. The battery is an alkaline battery of 0.5v, having enough energy to sustain the voltage level for a duration of 1500 minutes.

The pig 300 also includes a small panel LED (light emitting diode) allowing the pig 300 to indicate status to a programmer. The pig 300 also includes a small magnetometer for detecting the defect status of the internal surface of the pipeline 100 during its field run traversal thereof.

1.4 THE MAGLOGGER SYSTEM

Also shown in FIG. 1 are several magloggers, each placed at a known location external to, and in close proximity with, the pipeline. Basically, the elements or each maglogger such as 200*a* consist of the following at each of a sequence of logger reference points along the course of the pipeline network to be surveyed. A magnetic proximity detector having a fluxgate magnetometer 202, an analog-to-digital converter (ADC) 208, a maglogger clock 204, a recording device 206, and a microprocessor 210. Also, the maglogger 200 has an input 222 for connecting to a global positioning satellite (GPS) receiver 212. The maglogger 200 also contains a power source such as a battery 214. The maglogger contains a device for detecting the passage of the pig along the pipeline, and generates maglogger data when the passage of the pig along the pipeline is detected. The maglogger data includes either a magnetic detector such as a fluxgate magnetometer, or an accoustical device.

Before the field run, a portable computer system or other device having a GPS receiver is carried to the maglogger location and physically connected to the maglogger. The maglogger or the computer system records the location of the maglogger in GPS coordinates, allowing subsequent recovery of the maglogger location by a post-processing routine. Alternatively, each maglogger may have a global positioning satellite receiver for receiving signals from global positioning satellites such that the location of the maglogger is ascertainable in a terrestrial coordinate frame.

Figure 5B:
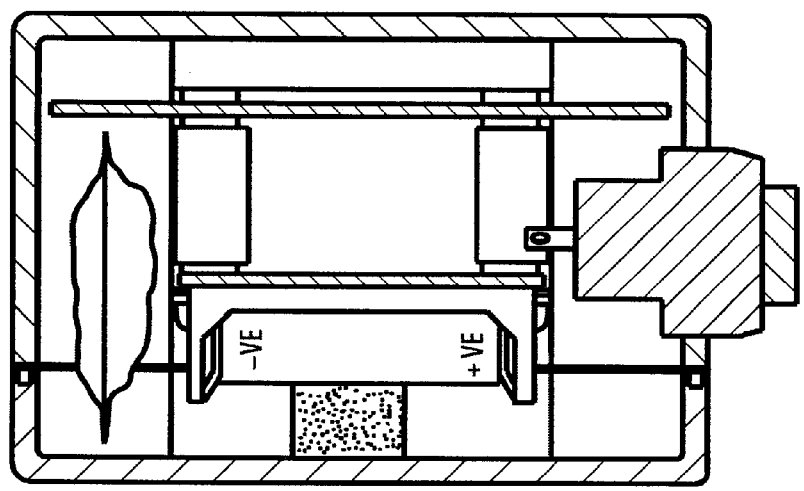
FIG. 5B is a cross-sectional view of the maglogger of FIG. 5A at an angle of 90° from the cross-sectional view of FIG. 5A.
Figure 5A:
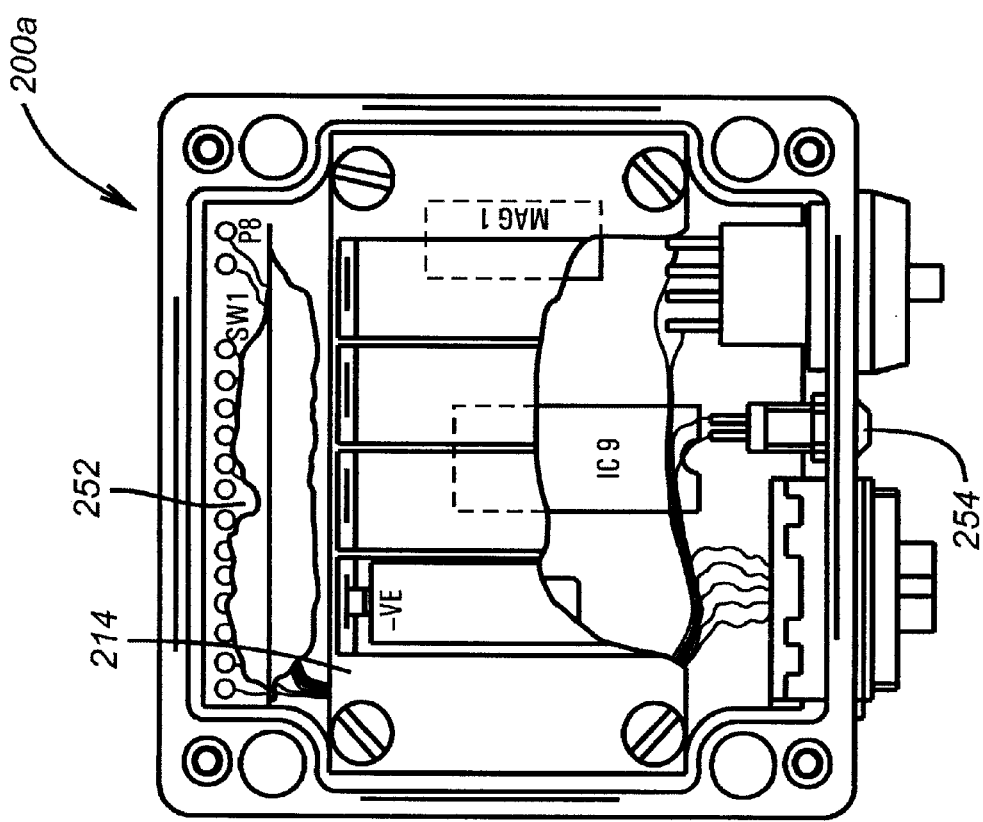
FIG. 5A is a cross-sectional view of a maglogger of the system of this invention.

Referring now to FIGS. 5A and 5B, one of the magloggers 200 is shown in greater detail. Because each of the magloggers 200*a*–200*f* is substantially identical, one maglogger 200 is explained in detail. Referring to FIGS. 5A and 5B, the magnetic proximity detector 202 detects the magnetic signature of the pig as it approaches and then recedes from the mgloger, i.e. the point where the off-board equipment is located. The magnetic proximity detector 202 contains a number of magnetic sensors, and in particular fluxgate magnetometers 202 that measure the overall ambient magnetic flux detected at the maglogger magnetic sensors. The magnetic flux detected by the maglogger changes as ferrometalic objects such is pipeline pig P passes the location of the maglogger. The fluxgate magnetometer 202 provides an analog signal, preferably a voltage, proportional to the overall ambient magnetic flux detected at the magnetic sensors.

It will be appreciated that the magnetic field strength increases as a ferrometalic object approaches and decreases as the object recedes. The pig contains a strong North Pole at one end and a strong South Pole at the other end, with a negligible magnetic field midway between the two ends. A zero crossing of the magnetic flux is a good approximation of the passage of the ferrometalic object.

Referring again to FIGS. 5A and 5B, an analog-to-digital converter (ADC) 208 receives the analog signal and provides a quantified value representing a highly precise approximation of the magnetometer output signal. The ADC 208 is a high-resolution converter providing up to 4090 values representing the voltage received. The large number of possible values allows high precision, and allows zero-crossings of the magnetic flux to be isolated even when the ambient magnetic flux is small.

Referring again to FIGS. 5A and 5B, the maglogger 200 also contains a microprocessor 210. The microprocessor 210 can be programmed, and indicates its program status via a light emitting diode (LED) 254.

Referring again to FIGS. 5A and 5B, the maglogger 200 also contains a highly precise clock 204, which provides an accurate measure of time, and is synchronized to the clock on-board the pig 300. The highly precise clock 204 within the maglogger provides a train of pulses at a predetermined data rate to a microprocessor 210, which also receives the output of the analog-to-digital converter 208. The clock 204 is derived from a temperature-compensated oscillator module 204*a* operating at 16.7 MHz, divided by two counters 204*b* to an operating frequency of 4.0 Hz.

Referring again to FIGS. 5A and 5B, the maglogger 200 also contains a recording device 206 that allows the clock output at the time of pig passage to be recorded for the subsequent data processing phase. The recording device 206 is a flash-ROM unit having cell-write/block-erase features allowing long-term nonvolatile data storage, and ease of block erasure. Using RAM 212, the microprocessor 210 executes a software process which creates a data structure within the recording device 206. The data structure within the recording device 206 may be understood as a data table recording the quantised, clocked output of the analog digital converter 208. The software process is a simple read-write process that receives the data from the ADC 208, increments an address pointer to an unused memory address, and stores the data in the recording devices 206.

Referring again to FIG. 1, the maglogger 200 position is recorded in a portable computer system that is carried to the maglogger before the pig is inserted into the pipeline. The maglogger and the portable computer system are coupled to a GPS receiver 212. Alternately, if desired, the maglogger 200 contains a port configured to be coupled to a GPS receiver. The portable computer system executes a routine that enables the portable computer system to create a file of all of the maglogger locations along the pipeline.

As will be recognized by one skilled in the art, various differential GPS location methods are well known, and provide a location to within a few centimeters. The GOPS receiver and antenna allows the maglogger 200 to receive information from a constellation of satellites

DIFFERENTIAL GPS

Referring again to FIG. 1, a reference location having a GPS sensor or receiver 400 defines an origin, or benchmark for the inertial reference frame. The reference location 400 is preferably a landmark from which distance to points along the pipeline may be measured. Directions such as north, east, and down define a right handed reference frame about the reference location 108 and provide a simple nomenclature for describing points along the pipeline. Located at the reference location 400, a GPS receiver similar to the GPS receivers 212 used to locate the magloggers 200 also receive signals from the global positioning satellites. The GPS receiver at the reference location records signals and the times at which signals are received. Consequently, subsequent post processing procedures analyzing GPS data from the reference location 400 and from the magloggers 200 can be used to determine chronological delays according to various differential GPS methods, these delays can be used to triangulate with great precession the location of each of the magloggers, since the signals are received at a known velocity (i.e., the speed of light).

Differential GPS allows a reference point at a precisely-known location (e.g., the fixed GPS sensor at location 400) and a second, roving GPS receiver (e.g., GPS receiver 108) to be connected over a UHF link to get rid of the noise, and to provide a very accurate estimate of the roving GPS receiver location. Such techniques are known in the art, and so will not be described herein in great detail.

1.5 THE OFF-SITE COMPUTER SYSTEM 400

Figure 6:
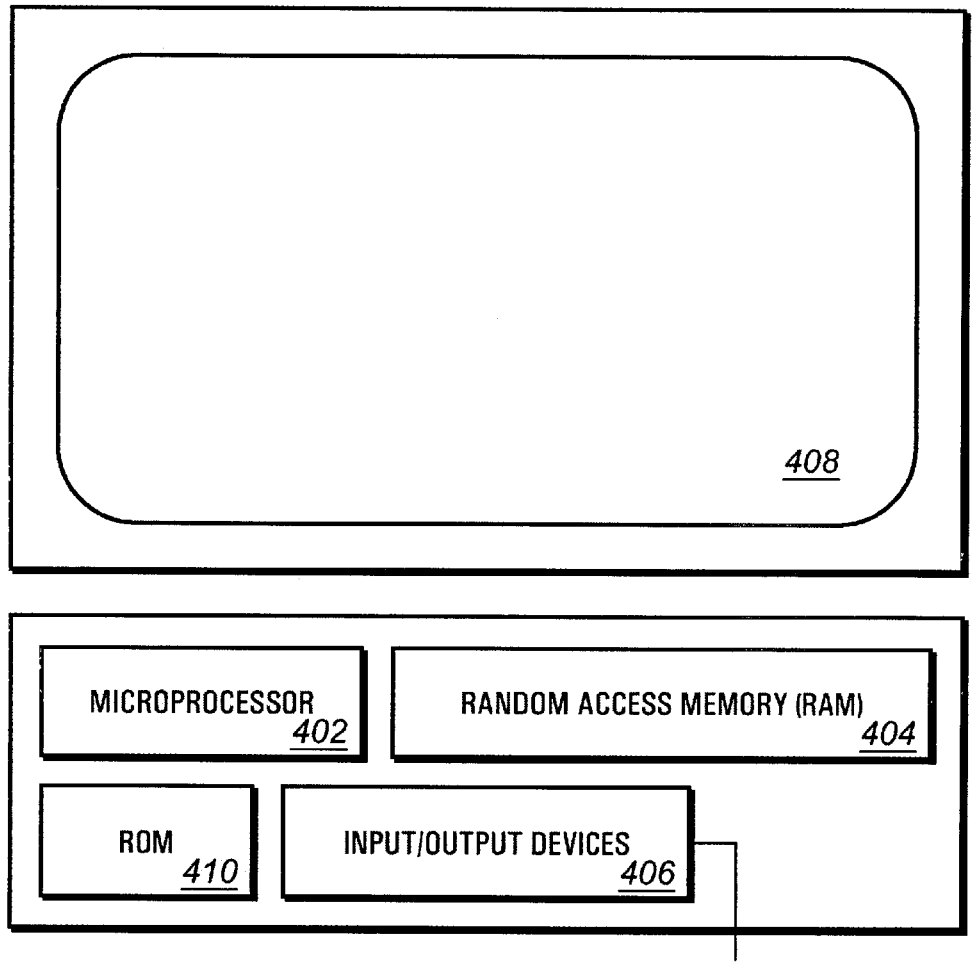
FIG. 6 is a schematic view of an off-site computer system.

Referring now to FIG. 6, an offsite computer system 400 is shown. The offsite computer system 400 includes a microprocessor 402, random access memory (RAM) 404, and input/output devices 406. Input/output devices 406 include input ports for receiving data from the recorder 316 within the inspection apparatus 302, and from the recording device 206 within the magloggers 200. Consequently, the input ports on the offsite computer system are configured accordingly. Output devices on the offsite computer system 400 include clock synchronizing pins configured to be coupled to the clock 314 in the inspection apparatus 302, and to the clocks 204 within the various magloggers 200a–200f. The output ports of the computer system 400 therefore allow synchronization among the various clocks in the pipeline pig field assembly shown in FIG. 1.

The offsite computer system 400 preferably further includes a video graphics display 408 for presenting the results of analysis of the recorded data obtained from the recorder 316 and recording device 206.

The offsite computer system 400 also includes a read only memory (ROM) 410, containing a set of instructions for processing data and for presenting resulting analysis of the analyzed data. The set of instructions are further described below with reference to FIGS. 7 and 8.

2.0 PRE- AND POST- PROCESSING

2.1 SETTING UP THE FIELD RUN

Figure 7:
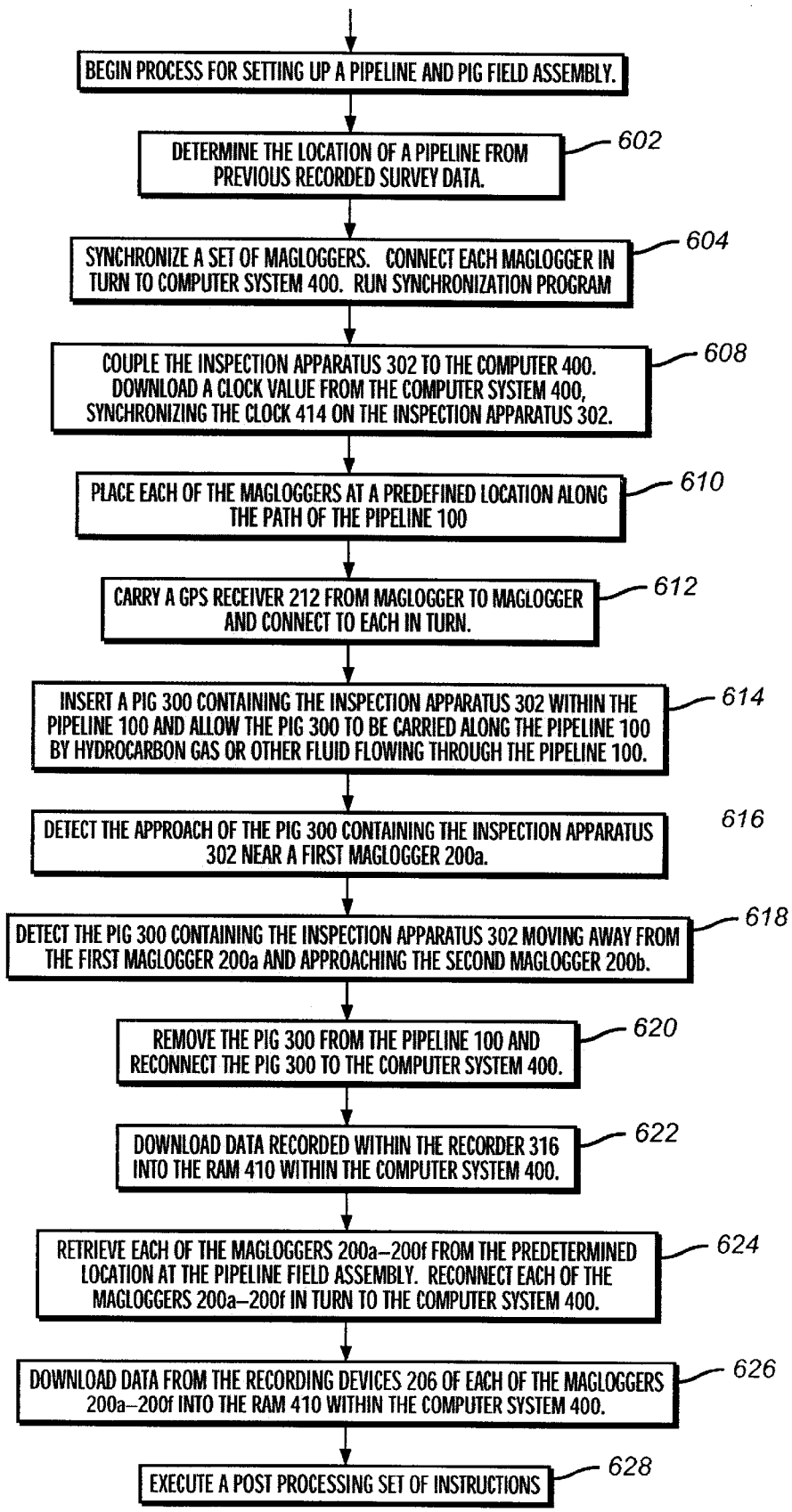
FIG. 7 is a schematic flow chart of the field run data acquisition process.

Referring now to FIG. 7, a process for setting up a pipeline and pig field assembly (of FIG. 1) is shown. A set of instructions for performing the steps indicated in FIG. 7 is stored within the ROM 410 of the offsite computer system 400, described in FIG. 6.

It is assumed that a survey map of the pipeline was created when the pipeline was put in place. At step 602, the location of a pipeline is determined from the previous recorded survey data. Various personnel identify locations along the path of the pipeline, space sufficiently apart, at which magloggers are to be located. At step 604 a set of magloggers are synchronized. Each maglogger in turn is connected computer system 400, and a special synchronization program run. The computer system 400 contains an internal clock, and the synchronization program reads a clock value from the internal clock, and provides the clock value to each of the magloggers. The clock value provides an initial starting point to the clocks 204 within the various magloggers 200a–200f. If desired, the magloggers 200a–200f may be simultaneously connected to different ports of the computer system 400, or may each be connected in turn. Thereafter, all the magloggers have synchronized clocks.

At step 608, the inspection apparatus 302 is coupled to the computer system 400. A clock value is again downloaded from the computer system 400, synchronizing the clock 414 on the inspection apparatus 302 to the clocks 204 within the magloggers 200a–200f. If desired, the inspection apparatus 302 may be connected simultaneously with the magloggers, or may be connected subsequently or previously.

Continuing to refer to FIG. 4, at step 610 each of the magloggers are placed at a predefined location along the path of the pipeline 100. The magloggers are located at least a predetermined distance from one another. At step 612, a GPS receiver 212 is carried from maglogger to maglogger and connected in turn. The GPS receiver 212 receives a signal from the global positioning satellites (GPS) in orbit around the earth. Each of the magloggers 200 records the GPS signal received from the global positioning satellites, and the time at which the GPS was received.

Because the magloggers are not moved once the position information from the GPS receiver 212 is downloaded, all data recorded by the maglogger recording device 206 is tagged with position information. Alternately, if desired, each maglogger 200a–200f may contain a GPS receiver for receiving signals from the GPS system.

At step 614, a pig 300 containing the inspection apparatus 302 is inserted within the pipeline 100 and allowed to be carried along the pipeline 100 by hydrocarbon gas or other fluid flowing though the pipeline 100. The inspection apparatus 302, as stated previously contains a battery 326 providing sufficient power to enable the various sensor devices on the inspection apparatus 302 to operate for a sufficient amount of time. The recorder 316 records data as the inspection apparatus moves along the pipeline.

Continuing to refer to FIG. 7 at step 616 the pig 300 containing the inspection apparatus 302 approaches a first maglogger 200a. The Fluxgate magnetometer 202 within the maglogger 200*a* is configured to measure the ambient magnetic flux in proximity to the maglogger 200*a*. Consequently, the approach of the pig 300 which has a ferromagnetic structure, is detected by the maglogger 200. Moreover, in the alternate embodiment in which a magnetic pulse generator 312 within the inspection apparatus 302 produces a substantial magnetic pulse whenever the odometer 304 reports a distance traveled that is a multiple of 3.3 meters, the instant at which the magnetic pulse is detected the fluxgate magnetometer 202 within the maglogger 200*a* is recorded. It will be remembered that the clock 204 within the maglogger 200*a* is synchronized with the clock 314 within the inspection apparatus 302. Consequently, the odometer 304 reports a distance traveled that may be correlated to the known maglogger location.

At step 618, the pig 300 moves away from the first maglogger 200*a* and approaches the second maglogger 200*b*. Consequently, the results in magnetic flux detected by the first maglogger 200*a* diminishes, while the magnetic flux recorded by the second maglogger 200*b* increases.

Each of the magloggers 200*a*–200*f* determines the magnetic flux strength and determines a zero-crossing point, to generate an instantaneous value of the pigs' closest approach. Each of the magloggers records the instant at which the pig was detected to have a closest approach, according to clock 204 within the maglogger 200.

At step 620, data from the pig 300 is transferred to the computer system 400. Mass storage media, such as tapes or other magnetic data storage devices, are transferred from the pig 300 to the computer system 400. Alternately, a portable computer system may be connected to the pig and the pig data downloaded, and the portable computer system transported to the computer system 400 and connected thereto for the data to be downloaded. Other means of data transfer may be used in the alternative or in conjunction with the forgoing. At step 622, data recorded within the recorder 316 is downloaded into the RAM 410 within the computer system 400. At step 624, each of the magloggers 200*a*–200*f* is retrieved from the predetermined location at the pipeline field assessably of FIG. 1, and reconnected in turn to the computer system 400. At step 852 data is downloaded from the recording devices 206 of each of the magloggers 200*a*–200*f* into the RAM 410 within the computer system 400. At step 628, a post processing set of instructions is executed.

The derivation of the logger reference-point positions assumes that the GPS information system has been processed in the most accurate manner possible. The derivation of the position of each logger reference point along the pipeline would normally be carried out by utilizing a differential approach in which the information obtained from a set of GPS measurements is processed as a batch. By so doing, all common errors (e.g.—those due to ionospheric and tropospheric refraction), which are essentially the same at each point, may be made to cancel out in the computation of the position of each reference point relative to all others in the grid of GPS-derived reference points.

The information processing concept used to derive precision pig position at all points along the course of the pipeline network is shown in FIG. 2. The information processing scheme uses the outputs of the IMU and odometer systems recorded during the real-time phase of the pipeline survey, in combination with the reference-point positions derived from the GPS measurements obtained during the pipeline survey, and the pig time of passage at each reference point.

2.2 POST-PROCESSING

As indicated, the operation of the system takes place in two phases: the real-time data collection and storage phase, and the off-line data processing phase. The real time data collection and storage phase, as depicted in FIG. 6 is carried out as the pig traverses the pipeline network. During this time data is collected from the inertial measurement unit and the odometer and recorded by the recording device. Also during this time, the time of passage of the pig at each logger reference point is recorded by means of a clock and recording device at each position, with each clock being synchronized to that on-board the pig. All data is time tagged using the on-board clock to allow later synchronization during the data post-processing phase.

Off-line reduction of the recorded data, together with the GPS-surveyed positions (latitude, longitude, altitude) of each logger leads to a set of four files (designated file 1, file 2, file 3, and file 4 in FIG. 7). These files provide the needed inputs for the post-processing phase.

FIG. 7 shows the data processing scheme that converts the data recorded and stored during the pipeline survey into a continuous set of 3-dimensional positions versus time. This position versus time data is correlated with magnetic pipeline inspection data also recorded during the real-time phase to allow pipeline features and faults to be precisely located for the purpose of cataloging the features, or for pipeline maintenance purposes.

Figure 8:
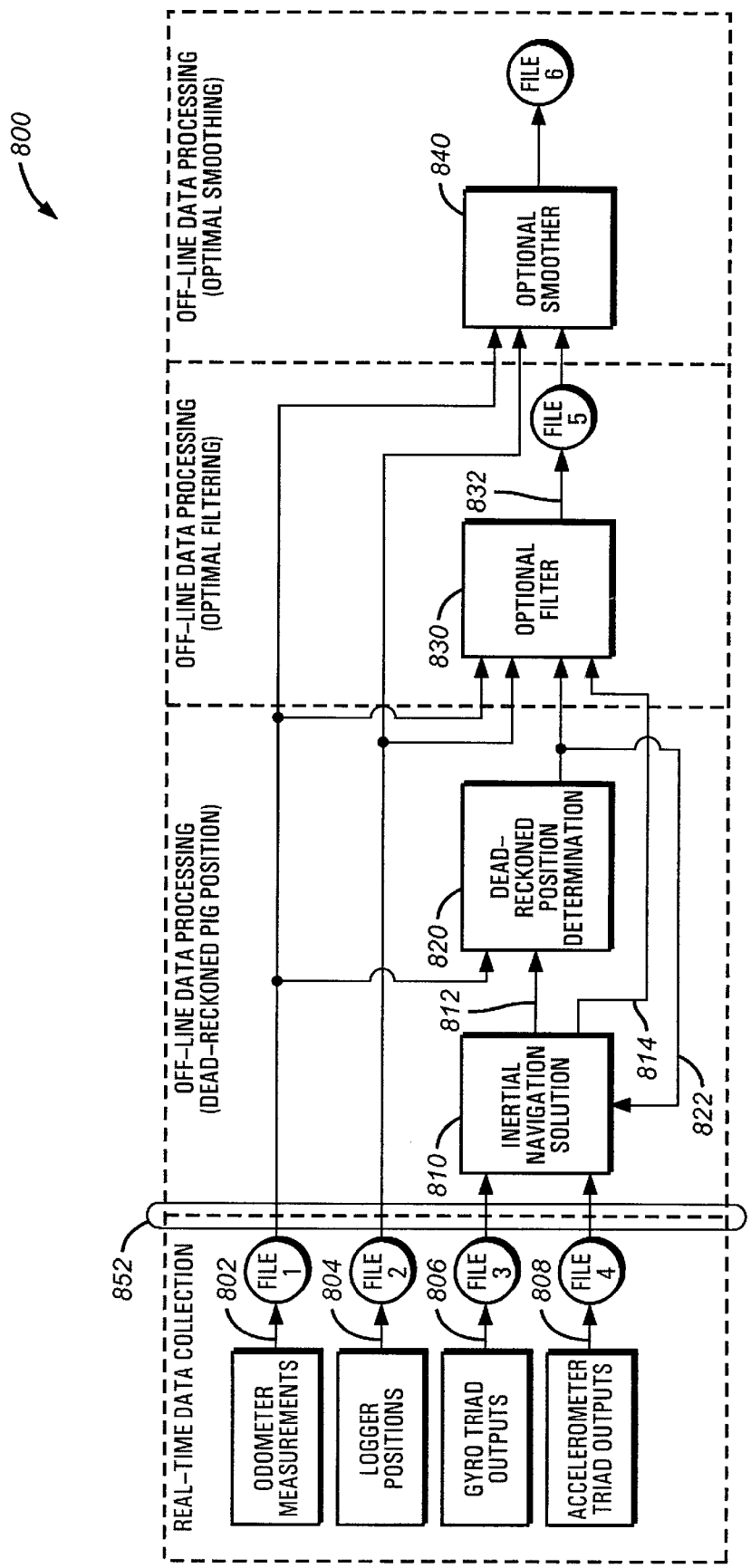
FIG. 8 is a chart of the System Information Collection and Processing Concept.

Referring now to FIG. 8, a block diagram showing various stages within the post processing phase is shown. Initially accelerometer triad outputs and gyro triad outputs stored as files 3 and 4, respectively, are downloaded from the recording device within the pig 300 into the computer system 400. The computer system derives an inertial navigation solution 810 comprising an attitude matrix and a velocity vector for the pig 300 at each data point within the files 1 and 2. The attitude matrix of the inertial navigation solution 810 represents the relationship between the pig-centered coordinate frame and a North/East/Down coordinate frame system.

It will be noted that the inertial navigation solution does not rely on any external velocity data, for example from an odometer; rather, the velocity vector and attitude matrix generated by the inertial navigation solution process 810 depends entirely on the IMU data, i.e. the gyro data and the accelerometer data. The velocity information is derived exclusively from the inertial measurement unit (IMU).

The odometer measurements, which are stored within the recording device 316 of the pig 300, are downloaded into the RAM of the offline computer system 400 as file 1. The dais from file 1 includes odometer measurements, tagged by clock timestamps. The odometer measurements and the attitude matrix, within the computer system 400, are provided to a dead reckoning position determination process 820. The dead reckoning position determination process 820 determines a position vector 822.

The initial pig heading allows the pig to be inserted within the pipeline 100 without substantial settling time. A "gyro compassing" or "north-finding" process is performed in the optimal filter of the post processing routines, as part of the optimal filter. Thus, time and battery power are saved, since much of the settling time before the pig is inserted into the pipeline is eliminated. As will be appreciated by those skilled in the art, inertial measurement units having gyros require substantial amounts of time, as much as an hour, for the inertial solution to settle to a precise orientation in inertial space before the pig 300 can be inserted into the pipeline. This settling time has typically been provided on battery power, reducing the amount of power available for the pigs traversal of the pipeline 100. Allowing the pig 300 to be inserted without the detrimental settling time requirements therefore enables the pig 300 to travel much further along a much longer pipeline 100. Although the gyro orientations have unknown initial conditions when inserted into the pipeline 100, the initial conditions can be calculated by the optimal filter in the post processing.

As further shown in FIG. 8, logger positions within the magloggers recorded 214 are downloaded into the RAM of the offsite computer system 400 as file 2. The logger positions, the position vector 822 and the velocity vector 814, as well as the odometer measurements of file 1, are provided to a optimal filter process 830. The optimal filter process 830 determines a best estimate of attitude matrix versus time and the odometer scale factor and bore sight errors. As described above, the odometer scale factor is caused by the gradual wear and tear on the odometer wheels, reducing the radius thereof. The bore sight error is a determination of the physical angle of misalignment between the inertial measurement unit 306 and the pig 300. The results of the optimal filtering process 830 are collected as file 5 within the RAM of the offsite computer system 400. Also shown in FIG. 8, an optimal smoother process 840 is included. The optimal smoother 840 receives the error estimates of file 5, the logger positions of file 2, and the odometer measurements of file 1 and computes a best estimate of pig position versus time. The best estimate of pig position versus time is calculated by "rewinding" the data of the various files and compensating for the errors identified in file 5.

Moreover, the optimal smoother process 840 is able to simulate a reverse transversal of the pipeline, in which the pig 300 is mathematically simulated to run in a reverse direction. The backward running allows several benefits. During a normal transversal of the pipeline 100, errors within the inertial measurement unit 306 and odometer apparatus 304 accumulate slowly. The accumulation of these errors reaches a maximum immediately before the pig encounters the next maglogger 200. At each maglogger, the true position is known and errors can be removed from that point forward. It will be recognized, therefore, that the maximum error is produced immediately before the next maglogger 200 is encountered. Advantageously, however, running the data in a reverse direction allows the errors to be cut approximately in half. In a reverse direction, each segment of pipeline, 100 between adjacent magloggers 200 begins with minimal error.

For example, adjacent magloggers 200a and 200b, time as the magloggers moves from the maglogger 200a to maglogger 200b, errors accumulate and reach a maximum immediately before maglogger 200b is encountered. The errors associated with points close to maglogger 200a have minimal error while the points near maglogger 200b have a maximum error. In reverse direction, however, the pig 300 is mathematically considered to have moved from maglogger 200b to maglogger 200a. At maglogger 200b, the pig position can be completely corrected using the true known location of maglogger 200b, although additional errors are considered to accumulate in route to maglogger 200a. By combining the forward and reverse directions, the accumulated errors have much less effect, and reach a maximum at a point approximately midway between the two magloggers. In each direction, an estimate of pig position versus time is computed by the optimal smoother 840, the various estimates are balanced in a Kalman filter processed within the optimal smoother 840.

Thus, the Kalman filter is run three times in succession, to allow the estimation of initial pig heading, the estimation of pig odometer scale factors and bore sight errors, and the estimation of pig attitude as a function of time.

As further shown in FIG. 8, the position vector 822 (including latitude) is provided to the inertial navigation solution process 810 to allow correction for earth-rate effects on the velocity vector.

The post-processing phase takes place in five stages. The functional modules that make up the data postprocessing concept implicit in FIG. 8 are defined in greater detail in the following paragraphs.

Referring now to FIG. 8, during the first stage the pig initial pitch and roll angles are approximately determined using a short segment of the inertial data contained in file 4, and the initial pig velocity approximately determined using a short segment of the odometer data contained in file 1. Subsequently, after rewinding files 1 and 4, the second stage commences and a fully aided navigation run is executed using the selected aiding capabilities. However, because the initial pig heading angle is unknown at the start of the second stage of the data post-processing, the Kalman Filter must be structured during this stage to include two unknown earth-rate components, $\Omega_x$ and $\Omega_y$. After processing on the order of one hour of data, the estimates of the two unknown earth rate components will be known with sufficient accuracy to allow the initial pig heading to be determined via the following equation $$\psi = \tan^{-1}\left(\frac{-\Omega_y}{\Omega_x}\right) \tag{50}$$

where $\psi$ is the desired pig heading angle relative to North at the start of the real-time data recording phase.

Referring again to FIG. 8, the third stage of the post-processing is dedicated to determining the odometer scale factor and boresight errors. These errors become observable via either the odometer measurement, or the dead-reckoned position change measurement between successive logger positions. Carrying out a fully aided navigation run leads to a set of estimates for these parameters to be used in the subsequent data post-processing, which are stored for subsequent use in file 5.

Referring again to FIG. 8, the fourth stage of the data post-processing is carried out by executing a fully aided navigation run in which the odometer data used in the dead-reckoned position determination are corrected prior to being used by applying the odometer scale factor and boresight error corrections derived in the third stage of the postprocessing. The aided-navigation run produces the best estimate of the pig attitude matrix at a sequence of points spanning the pipeline network being surveyed, at a spacing of a fraction of a meter. The dead-reckoned position is re-initialized using the known logger position as each successive logger is reached. The attitude information is stored in file 5 for subsequent use in the data post-processing.

The fifth stage of the data post-processing is carried out for each logger interval in succession by executing a dead-reckoned position computation starting from the known position (latitude, longitude, altitude) of the first logger and advancing to the second logger. Then, initializing the dead-reckoned position to that of known position of the second logger, the dead-reckoning process is once again executed in a reverse sense using the stored attitude matrix and odometer data until the first logger point is reached. The forward and reverse dead-reckoned positions are combined in the optimal smoothing algorithm to produce the best estimate of the pig position at all interior points between the first and second loggers. Since the smoothing process takes place on rectilinear position data, the specification of the latitude and longitude at each interior point between the first and second loggers is carried out using the following conversion equations:

$$\hat{\lambda}_n = \lambda(N-1) + \frac{\hat{x}_{north}(n)}{\mu_n + h} \quad (51)$$

$$\hat{\Lambda}_n = \Lambda(N-1) + \frac{\hat{x}_{east}(n)}{(\mu_e + h)\cos\lambda_{avg}} \quad (52)$$

where $\hat{\lambda}_n$, $\hat{\Lambda}_n$=optimally smoothed estimates of latitude and longitude at the $n^{th}$ interior point between the $(N-1)^{th}$ and $N^{th}$ loggers $\lambda(N-1), \Lambda(N-1)$=known latitude and longitude of the $(N-1)^{th}$ logger $\hat{x}_{north}(n), \hat{x}_{east}(n)$=optimally smoothed North and East position estimates at the $n^{th}$ interior point between the $(N-1)^{th}$ and $N^{th}$ loggers $\mu_n$, $\mu_e$=earth's principal radii of curvature in North and East direction, respectively $\lambda_{avg}$=average latitude over logger interval Once the latitude, longitude, and altitude have been determined at all of the interior points between the two loggers, these values together with the time associated with each point is stored in file 7.

The fifth stage of the data post-processing is repeated until all logger intervals spanning the course of the pipeline network have been processed

2.2.1 THE FIRST PHASE: DOWNLOADING AND PROCESSING OF RAW DATA MEASUREMENTS

Referring again to FIG. 8, as stated previously, data is recorded within the magloggers and within the inspection apparatus within the pig. In the first phase of the post processing routines, the data is downloaded in step 852 into the off-site computer and processed.

The data sources also include a clock which provides an accurate measure of time, and is synchronized to the clock on-board the pig. The clock is highly precise and determines not only when the passing of the pig is detected, but also when a particular signal from a CPS satellite is received. The clock is pre-synchronized to a similar clock within the off-site computer 400.

The data sources also include a clock located within the inspection apparatus 302 within the pig 300. The clock provides accurate absolute time to be used in the subsequent data processing phase as the means of synchronizing all of the on-board and off-board measurements.

The data sources also include a recording device on board the pig, that allows the IMU, odometer, and clock outputs to be recorded at a rate sufficient for the needs of the subsequent data processing phase. The recording device further includes a data port for downloading a data file (or a set of data files) from the inspection apparatus 302 within the pig 300 to the off-site computer system 400.

The data source also include a recording device within each maglogger, that allows the clock output at the time of pig passage to be recorded for the subsequent data processing phase.

The recording device of the inspection apparatus contains the IMU and odometer data in one or more data files, which are downloaded and processed. The recorder of the magloggers each contain a data file that contains the timing of the passing of the pig. Each of these data files is downloaded to the off-site computer system 400 and processed.

2.2.1.1 The IMU

The data sources include an Inertial Measurement Unit (IMU) consisting of a triad of gyros, a triad of accelerometers, and a digital processor that compensates the sensor outputs, and converts them into a form suitable for storage. The IMU is located within the inspection apparatus 302 within the pig 300.

The IMU data contains six data values for each data clock cycle. It will be remembered that the data clock cycle is 0.02 seconds, corresponding to 50 Hz.

The IMU data contains the acceleration in each of the three measured directions, at each clock cycle. The acceleration data is the set of values obtained from the accelerometers via the analog-to-digital converter within the pig during its transversal of the pipeline.

Also, the IMU data contains three incremental angles, representing the change in pig orientation over the clock cycle. The latter would, for example, be suitable for integrating, to determine the absolute orientation of the pig. Instead, however, the raw gyro data representing "delta" or incremental angle changes is what is stored in the data file.

2.2.1.2 THE PIPELINE DEFECT/ANOMOLY INSPECTION APPARATUS

2.2.1.3 THE ODOMETER

The data sources also include an odometer that measures the distance traveled by the pig along the course of the pipeline. The odometer is located within the inspection apparatus 302 within the pig 300. Data from the odometer is downloaded from the recording device 316, after the field test is run, into the computer system 400.

Referring again to File 1 shown in FIG. 8, as stated above, the odometer is a device that measures distance traveled via the observed incremental rotations of a precisely machined set of wheels. The measurement system is typically configured using three individual wheels that are at 120 degree separations relative to each other around the circumference of the pig. The availability of three measurements of distance traveled allows averaging to enhance the accuracy of the measurement. In addition, further enhancements to the accuracy of the odometer measurements may be achieved by accounting for the effect of wheel castoring on the measurement of distance traveled. This is accomplished using the inertial system to compute the castoring angle, which may then be used to adjust the readings obtained from each odometer wheel.

The wheels will each castor by the same angle when the pig rotates about its roll axis. It is not difficult to show that the castor angle is defined by the following equation $$\gamma = \tan^{-1}(r_p \dot{\phi}/v) \quad (39)$$

where $\gamma$=castor angle $\dot{\phi}$=roll rate of pig $r_p$=radius of pipeline $v$=speed of pig The roll rate, ϕ̇, and speed, v, of the pig needed in computing the castor angle are obtained directly from the inertial solution. Once the castor angle is known, the incremental distance indicated by a given odometer wheel over a given time interval may be corrected according to $$\Delta\hat{s} = \Delta s \cos\gamma \qquad (40)$$

where $\Delta\hat{s}$=corrected value of incremental distance traveled $\Delta s$=incremental distance registered by odometer wheel Continuing to refer to File 1 of FIG. 8, the odometer yields directly a measurement of the incremental distance traveled, along an arc length of the pipeline, over a given time interval. However, two other implicit measurements that are commonly utilized in odometer-based systems account for the fact that, in an average sense, the vehicle experiences no net motion in the lateral and normal directions, but only in the axial direction. These two addition measurements are commonly referred to as "zero side-slip" and "zero up-slip" measurements. For the set of three measurements (axial, lateral and normal) the difference is formed with respect to the inertially-derived values of these same quantities.

The odometer measurement vector is explicitly defined by $$y = \begin{bmatrix} y_1 \\ y_2 \\ y_3 \end{bmatrix} = \begin{bmatrix} \int_{t_{j-1}}^{t_j} V \cdot u_1 dt - (s_j - s_{j-1}) \\ \int_{t_{j-1}}^{t_j} V \cdot u_2 dt \\ \int_{t_{j-1}}^{t_j} V \cdot u_3 dt \end{bmatrix} \qquad (41)$$

where V is the inertially derived velocity vector, and the $u_i$ are unit vectors defining the pig body axes, and which are directly defined by the columns of the direction cosine matrix C.

Each measurement will have a nominal value of zero, but in actuality will have a nonzero value due to the residual errors in the information entering the measurement relationship, and the measurement noise itself. A discretized set of odometer measurement error equations suitable for use in the Kalman Filter, that accounts for the direct along-track measurement of incremental distance traveled, and the implicit zero side-slip and zero up-slip measurements, is defined by $$y_1 = s_{11}\delta V_n(j) + s_{12}\delta V_e(j) + s_{13}\delta V_d(j) + k\Delta s(j) + \xi_1(j) \qquad (42)$$

$$y_2 = s_{12}V_n(j) + s_{22}\delta V_e(j) + s_{32}\delta V_d(j) + \alpha\Delta s(j) + \xi_2(j) + g_{13}\psi_n(j) + g_{23}\psi_e(j) + g_{33}\psi_d(j) \qquad (43)$$

$$y_3 = s_{13}\delta V_n(j) + s_{23}\delta V_e(j) + s_{33}\delta V_d(j) + \beta\Delta s(j) + \xi_3(j) - g_{12}\psi_n(j) - g_{22}\psi_e(j) - g_{32}\psi_d(j) \qquad (44)$$

where the $s_{ij}$ and $g_{ij}$ are defined by $$s_{ij} = \int_{t_{j-1}}^{t_j} c_{ij} dt$$

$$g_{ij} = \int_{t_{j-1}}^{t_j} sc_{ij} dt$$

and in which $y_1$=error in axial measurement (difference between the integrated axial inertial velocity, and incremental odometer output over the $j^{th}$ measurement interval)

$y_2$=error in lateral measurement (difference between the integrated lateral inertial velocity, and the nominally zero value for this quantity, over the $j^{th}$ measurement interval)

$y_3$=error in normal measurement (difference between the integrated normal inertial velocity, and the nominally zero value for this quantity, over the $j^{th}$ measurement interval)

$\xi_1(j)$, $\xi_2(j)$, $\xi_3(j)$=random measurement errors in $y_1$, $y_2$, and $y_3$ $\psi_n(j)$, $\psi_e(j)$, $\psi_d(j)$=components of attitude error vector $\delta V_n(j)$, $\delta V_e(j)$, $\delta V_d(j)$=components of velocity error vector k=odometer scale factor error α,β=boresight errors in lateral and normal directions $c_{ij}$=elements of attitude matrix $t_j$=time corresponding to the end of the measurement interval $t_{j-1}$=time corresponding to the start of the measurement update $\Delta s$=along-track incremental distance traveled over measurement time interval ṡ=along-track velocity The set of three measurements are processed by the Kalman Filter at a time interval on the order of 5 seconds, during which time the pig will have traveled a distance of on the order of 15 to 20 meters.

2.2.1.4 THE MAGLOGGER

The data sources also include a GPS receiver and antenna within each maglogger for receiving information from a constellation of satellites, which is used during an initial survey phase and then removed. The GPS receiver is connected to each maglogger when the maglogger is in location near the pipeline, and records the signals from the GPS satellites orbiting the earth, recording the time at which each signal is received. As long as the maglogger is not moved, and as long as the a reference GPS receiver is operational to receive the same signal at a slightly different point in time (the difference in time being due to the distance between the GPS receivers), the GPS receiver need not be reconnected to the maglogger. Maglogger data is downloaded from recorder 216 into computer system 400 after the field test is run.

The data sources also include a magnetic proximity detector which detects the magnetic signature of the pig as it approaches and then recedes from the point where the off-board equipment is located. The magnetic proximity detector indicates precisely when the zero-crossing of the magnetic flux (i.e., the derivative of the magnetic field strength) occurs. Maglogger data is downloaded from the recorder 216 into computer system 400 after the field test is run.

DETERMINING THE MAGLOGGER LOCATION

Referring again to FIG. 8, and in particular to File 2, as indicated above, a reference location off-site has a GPS receiver that receives signals from several GPS satellites and records the times at which each signal is received. Examining the GPS signals at each maglogger for identical signals, the differences in times at which the signals are received can be used in a differential GPS algorithm to triangulate precisely where each maglogger was located. Thus, the maglogger locations are known highly precisely. The accuracy of the overall pipeline survey will clearly depend on the frequency and accuracy of the logger position data.

Since the accuracies of the logger positions are critical to the overall accuracy achievable in the pipeline survey, it is important to understand the nature of the error in the logger positions. Two components of logger position error may be distinguished: absolute error, and relative error. The absolute error may be defined as a common error that affects each logger position by essentially the same amount (each logger in the network is in error relative to an absolute frame of reference by a fixed amount), while the relative error affects each logger position in relationship to all other loggers by an amount which is random and unique to that logger. This separation of the total error into two components is useful in defining an error specification for the system, and is also consistent with the errors incurred in a Differential GPS survey of the logger positions, which is the preferred technique to be utilized.

Referring again to File 2 shown in FIG. 8, the relative positions of the logger positions may be established very accurately (to within a few centimeters) if the GPS survey is carried out in a differential mode, and baselines less than about 25 km are maintained. This, can take two forms: (a) using a mobile receiver and a fixed reference receiver, with radio communication between the fixed and mobile elements and, (b) collecting and recording satellite data from two points in the logger network simultaneously (one of which has already been surveyed using GPS), and postprocessing. In both cases the position errors due to satellite ephemeris error, and ionospheric and tropospheric refraction errors are common to both receivers and, therefore, the determination of relative positions between receivers will be possible to a very high degree of accuracy. If all loggers in the pipeline network are surveyed in the differential mode, the relative positions of all points will be known to within a few centimeters. However, the absolute position accuracy of the pipeline network will be known to a much lesser accuracy (around 10–20 meters) unless one point in the network has been established with a greater accuracy. This in fact is possible if a GPS receiver is set up at a master reference point, and GPS data gathered over a number of hours is processed. By this means, the absolute accuracy of the pipeline network may be increased to on the order of a few tenths of a meter or better.

A logger error model, suitable for use in the optimal filtering process, is one where each of the three components of the 3-dimensional logger relative position error is treated as a purely random (zero-mean) measurement error that is uncorrelated with the other two relative position errors. Two distinct methods of utilizing the logger information are possible, as described in the following.

Referring now to FIG. 8, and in particular to a dead-reckoning process 820, in the first realization, the logger 3-dimensional measurement of position is filtered with that obtained from the dead-reckoned solution to arrive at a set of position error measurements to be utilized in the Kalman Filter. A set of discretized measurement relationships suitable for this purpose are defined by:

$$y = \begin{bmatrix} y_4 \\ y_5 \\ y_6 \end{bmatrix} = \begin{bmatrix} R_n(N) - R_n(N-1) \\ R_e(N) - R_e(N-1) \\ R_d(N) - R_d(N-1) \end{bmatrix} - \begin{bmatrix} X_n(N) - X_n(N-1) \\ X_e(N) - X_e(N-1) \\ X_d(N) - X_d(N-1) \end{bmatrix} \quad (45)$$

where
$R_n(N)$, $R_e(N)$, $R_d(N)$=dead reckoned NED position components at the $N^{th}$ logger position
$X_n(N)$, $X_e(N)$, $X_d(N)$=NED position components of the $N^{th}$ logger position The measurement error equation follows directly as $$\begin{bmatrix} y_4 \\ y_5 \\ y_6 \end{bmatrix} = \begin{bmatrix} \delta R_n(N) - \delta R_n(N-1) \\ \delta R_e(N) - \delta R_e(N-1) \\ \delta R_d(N) - \delta R_d(N-1) \end{bmatrix} + \begin{bmatrix} \xi_4(N) \\ \xi_5(N) \\ \xi_6(N) \end{bmatrix} \quad (46)$$

where
$\delta R_n(N)$, $\delta R_e(N)$, $\delta R_d(N)$=components of the NED dead-reckoned position error vector at the $N^{th}$ logger position
$\xi_4(N)$, $\xi_5(N)$ and $\xi_6(N)$=random NED measurement errors in the $N^{th}$ logger position relative to the $(N-1)^{th}$ logger position Continuing to refer to process 820 of FIG. 8, because the dead-reckoned position is started anew at each successive logger the errors at the $(N-1)^{th}$ logger can be treated as identically zero, with any residual error being absorbed into the random measurement noise—which leads to a modified measurement error equation as $$\begin{bmatrix} y_4 \\ y_5 \\ y_6 \end{bmatrix} = \begin{bmatrix} \delta R_n(N) \\ \delta R_e(N) \\ \delta R_d(N) \end{bmatrix} + \begin{bmatrix} \xi_4(N) \\ \xi_5(N) \\ \xi_6(N) \end{bmatrix}$$

In the second realization, the logger 3-dimensional measurement of position is compared to that obtained from the inertially derived change in position between successive loggers to arrive at a set of position error measurements to be utilized in the Kalman Filter. A set of discretized measurement relationships suitable for this purpose are defined by:

$$y = \begin{bmatrix} y_7 \\ y_8 \\ y_9 \end{bmatrix} = \begin{bmatrix} r_n(N) - r_n(N-1) \\ r_e(N) - r_e(N-1) \\ r_d(N) - r_d(N-1) \end{bmatrix} - \begin{bmatrix} X_n(N) - X_n(N-1) \\ X_e(N) - X_e(N-1) \\ X_d(N) - X_d(N-1) \end{bmatrix} \quad (47)$$

where $r_n(N)$, $r_e(N)$, $r_d(N)$ are the inertially derived NED positions at the $N^{th}$ logger position. The inertially derived position changes are derived by integrating the inertial velocities while the pig is traversing the pipeline segment between the $(N-1)^{th}$ and $N^{th}$ logger positions or, explicitly $$r_n(N) - r_n(N-1) = \int_{t_{N-1}}^{t_N} V_n dt$$

$$r_e(N) - r_e(N-1) = \int_{t_{N-1}}^{t_N} V_e dt$$

$$r_d(N) - r_d(N-1) = \int_{t_{N-1}}^{t_N} V_d dt$$

The measurement error equation for this set of measurements is as follows $$\begin{bmatrix} y_7 \\ y_8 \\ y_9 \end{bmatrix} = \begin{bmatrix} \delta r_n(N) - \delta r_n(N-1) \\ \delta r_e(N) - \delta r_e(N-1) \\ \delta r_d(N) - \delta r_d(N-1) \end{bmatrix} + \begin{bmatrix} \xi_7(N) \\ \xi_8(N) \\ \xi_9(N) \end{bmatrix} \quad (48)$$

However, as was true for the dead-reckoned position change measurement equations, the inertially derived position can be treated as perfectly known at the $(N-1)^{th}$ logger, with any residual error being absorbed into the random measurement noise—which leads to the following measurement error equation $$\begin{bmatrix} y_7 \\ y_8 \\ y_9 \end{bmatrix} = \begin{bmatrix} \delta r_n(N) \\ \delta r_e(N) \\ \delta r_d(N) \end{bmatrix} + \begin{bmatrix} \xi_7(N) \\ \xi_8(N) \\ \xi_9(N) \end{bmatrix} \quad (49)$$

For either the first or second realization of the logger position measurement, the measurement is processed by the Kalman Filter only upon reaching a logger, which will at typical pig velocities and logger spacings be at a time interval on the order of 15 to 20 minutes.

The three sets of measurement equations defined by (42), (43), (44), (46), and (49) can each be defined in the form $$y = HX + \xi$$

where H is the measurement matrix for the set of measurements, and $\xi$ is the measurement noise vector having the measurement error covariance matrix, R.

2.2.2 DETERMINING THE ATTITUDE MATRIX AND THE VELOCITY VECTOR: THE INERTIAL NAVIGATION SOLUTION

Referring now to the Inertial Navigation process 810 of FIG. 8, the IMU gyro 306 and accelerometer data are integrated to provide an inertial navigation solution in the North/East/Down frame consisting of an attitude matrix and a 3-dimensional velocity vector. Each gyro output consists of a sequence of incremental attitude angles, and each accelerometer output consists of a sequence of incremental velocities. The pig position in the North/East/Down frame is provided from the Dead-Reckoned Position Determination Module to allow the earth-rate and transport rates required in the Inertial Navigation Solution. This operation is carried out at a nominal 50-hz iteration rate.

The function of the Navigation Equation Module is to convert the recorded incremental angles and velocities from the inertial sensor triad into a pig attitude matrix and velocity vector. The inertial navigation solution also requires a set of initial conditions, and a gravity model.

In general terms, an inertial navigation system functions by continuously measuring the components of vehicle non-gravitational acceleration and angular velocity in three orthogonal sensor reference axes and, simultaneously, integrating the set of differential equations defining vehicle attitude, velocity, and position that have these measurements as inputs. The errors in the navigator's outputs arise principally from three sources: initial condition errors, errors in the inertial sensor measurements, and errors associated with the assumed earth gravity model.

In the pipeline surveying application the strapdown solution, as expressed in a North/East/Down (NED) coordinate frame, is defined by an attitude matrix that provides the transformation between the sensor reference frame and the NED frame, and a velocity vector. The equations solved in the Navigation Equation Module are the following:

$$\dot{C} = C\{\omega\} - \{\Omega + \rho\}C \quad (1)$$

$$\dot{V} = CA - \{2\Omega + \rho\}V + g \quad (2)$$

where

C=transformation matrix from sensor reference frame to local-vertical NED frame, with initial condition C(0)

V=velocity vector in NED frame, with initial condition V(0)

$\Omega$=angular velocity vector of earth with respect to the inertial frame $\rho$=angular velocity of local-vertical frame with respect to the earth reference frame $\omega$=angular velocity vector of sensor reference frame with respect to the inertial frame A=nongravitational acceleration vector of vehicle g=plumb-bob gravity vector and the convention is used here and throughout that a quantity of the form, {V}, denotes the skew-symmetric matrix formed from the components, $v_i$, of the enclosed vector, v.

The Inertial Navigation Module 810 shown in FIG. 8 requires inputs from the odometer, and position information from the Dead-Reckoned Position Module. This allows the earth rate and transport rate vectors to be computed via $$\Omega = \begin{bmatrix} \Omega_n \\ \Omega_e \\ \Omega_d \end{bmatrix} = \begin{bmatrix} \omega_e \cos\lambda \\ 0 \\ -\omega_e \sin\lambda \end{bmatrix} \quad (3)$$

$$\rho = \begin{bmatrix} \rho_n \\ \rho_e \\ \rho_d \end{bmatrix} = \begin{bmatrix} \dot{s} c_{21}/(\mu_e + h) \\ -\dot{s} c_{11}/(\mu_n + h) \\ -\dot{s} c_{21}\tan\lambda/(\mu_e + h) \end{bmatrix} \quad (4)$$

where $\Omega_n$, $106_e$, $\Omega_d$=earth-rate components in NED frame $\rho_n$, $\rho_e$, $\rho_d$=transport-rate components in NED frame $\omega_e$=earth's rotation rate relative to an inertial frame of reference $\lambda$=geodetic latitude $\mu_n$, $\mu_e$=earth's principal radii of curvature in North and East directions h=altitude $c_{ij}$=elements of the attitude reference matrix, C In the pipeline inspection application, it is desirable to eliminate the requirement for a ground alignment phase, which is a technique typically used in inertial navigation system applications to determine the initial attitude matrix, C(0), in a known zero-velocity environment. An alternative approach, delineated in the subsequent discussion, allows the attitude matrix to be initialized "on-the-fly" using the available aiding information from the odometer and loggers in a first pass through the recorded data. The unknown initial value, V(0), of the velocity vector may be determined in a similar manner using the odometer measurement together with the output of the accelerometer triad during a coarse initialization phase.

2.2.3 USING DATA FILES TO DETERMINE PIG POSITION: DEAD-RECKONED POSITION DETERMINATION

Referring again to FIG. 8, and particular to process 810, the attitude information derived in the Inertial Navigation Solution may be combined with the odometer data collected and stored during the real-time phase of the survey to derive pig position at all points in the pipeline network. The use of "dead reckoning" to compute position is carried out by resolving the instantaneous increment of pig travel along the arc of the pipeline during each small time interval, using the instantaneous attitude matrix, thereby determining the increment of pig travel in a geographic North/East/Down reference frame and then, summing these increments, the pig position coordinates in this reference frame are obtained. This operation is carried out at a nominal 50-hz iteration rate.

The function of the Dead-Reckoning Position Module 820 of FIG. 8 is to compute the location of the pig in a North/East/Down reference frame using the accurate attitude information that is available from the Inertial Navigation Module, together with the incremental output of the odometer. The basic position differential equation is defined by $$\dot{R} = C\dot{s} \tag{5}$$

where

R=3-dimensional position vector, in a North/East/Down frame $\dot{s}$=rate of change of distance traveled and C is the instantaneous attitude matrix available from the solution of (1). A discrete update equation for the variation of the dead-reckoned position vector is given by $$R_n = R_{n-1} + C_n \Delta s_n \tag{6}$$

in which $\Delta s_n$ is the incremental odometer output vector, nominally defined by $$\Delta s_n = \begin{bmatrix} s_n - s_{n-1} \\ 0 \\ 0 \end{bmatrix} \tag{7}$$

and $R_n$=position vector in NED frame at the end of the $n^{th}$ iteration interval $C_n$=attitude matrix at the end of the $n^{th}$ iteration interval $s_n$=odometer output at the end of the $n^{th}$ iteration interval The nominally defined odometer output vector is modified in the following manner to account for known corrections for odometer scale factor and boresight errors $$\Delta \hat{s}_n = \begin{bmatrix} (1-\hat{k}) \\ \hat{\alpha} \\ \hat{\beta} \end{bmatrix} (s_n - s_{n-1}) \tag{8}$$

where $\Delta \hat{s}_n$=corrected incremental odometer output vector $\hat{k}$=odometer scale factor correction $\hat{\alpha}, \hat{\beta}$=odometer boresight corrections with the odometer scale-factor and boresight corrections having been derived by the optimal filtering process during a preliminary pass through the data.

2.2.4 DETERMINING ERRORS: THE OPTIMAL (KALMAN) FILTER

Since the inertial navigation solution, consisting of the inertially derived attitude matrix 812 and velocity vector 814, and the dead-reckoned derived position vector 822 will be degraded over time due to sensor biases and random noise, and odometer scale-factor and boresight errors, aiding information must be periodically incorporated to correct the inertial navigation solution. The correction applied to the solution is derived using an optimal filtering approach, which can utilize information from both the logger reference positions and the odometer. The optimal filter 830 produces corrections to the pig attitude matrix 812 and velocity vector 814, and an estimate of the odometer scale factor and boresight errors 832. This operation is carried out at a nominal iteration interval of 2 to 5 seconds for odometer measurement processing, and at a nominal interval of 15 to 20 minutes for logger position measurement processing.

The function of the Optimal Filter Module 830 shown in FIG. 8 is to process measurements consisting of the difference between quantities derived from the odometers and loggers, and the corresponding quantities derived from the inertial navigation solution. The Kalman Filter structure is such that all information is blended (i.e., integrated) in an optimal fashion, and is closely related to the more familiar concept of recursive least-squares estimation. Effective use of the Kalman Filter requires knowledge of the following important elements:

A model for the dynamic variations in the state (in our case, the errors in the inertial navigation solution for attitude and velocity, and the dead-reckoned position). This takes the form of a set of differential or difference equations A model for the constant and random errors that act as the forcing functions to the dynamic state (in our case, gyro and accelerometer biases and random-walk errors)

A model for the constant and random errors that appear in the aiding information (in our case, the errors in the position measurement obtained from the loggers, and the odometer scale-factor, boresight, and random slippage errors ).

The outstanding attribute of the Kalman Filter is that it allows all of the above elements to be accounted for in a very systematic and formalized way, which makes it ideal for implementation in a digital computer. The following discussion summarizes the steps implicit in the implementation of the Kalman Filter.

2.2.4.1 KALMAN FILTERING THEORY

Consider a system whose behavior is defined by the following set of discrete linear equations:

$$X_n = \Phi_n X_{n-1} + B_n \eta_n \tag{9}$$

where

X=vector of states $\eta$=vector of random (zero-mean) noise sequences $\Phi_n$=state transition matrix from $(n-1)^{th}$ to $n^{th}$ update points $B_n$=noise distribution matrix For a given $\Phi$ and B, the state X will have a time variation determined by the particular noise sequence, $\eta$, and initial condition, $X_0$, which in general is taken to be a randomly distributed quantity. Since the noise sequence, $\eta$, has an infinite number of realizations, and the initial condition error can assume an infinite number of values, the system given by (9) has an infinite number of solutions. Because this is true, attention must be focused on the statistical behavior of Equation (9) rather than on specific solutions.

The most natural and useful way of characterizing the behavior of (9) is to compute the statistical parameters that define the bounds on the state vector, X. The statistical bounds on the components of X are found by solving the covariance matrix equation associated with (9), which takes the recursive form:

$$P_n = \Phi_n P_{n-1} \Phi_n^T + B_n Q_n B_n^T \tag{10}$$

where P is the error covariance matrix of the state vector, X, defined explicitly by:

$$P = [P_{ij}]$$

and $$P_{ij} = E(x_i x_j)$$

in which E denotes the expectation operator. It is seen that the individual variances of the components of X are defined by the diagonal elements of P, with the joint expectations being defined by off-diagonal elements of P. The matrix Q in (10) is the covariance matrix of the driving noise vector, $\eta$, defined by:

$$Q=[q_{ij}]$$

in which $$q_{ij}=E(\eta_i\eta_j)$$

Consider the case where the discrete process defined by (9) represents the trite dynamic propagation characteristics associated with a given linear system. For this case, assume that a measurement is made at the nth measurement update time employing an external measuring device which allows a specific linear combination of the states to be directly monitored. A general way of stating this in mathematical terms is as follows:

$$y_n = H_n X + \xi_n \quad (11)$$

where $y_n$=vector of measurements $H_n$=measurement matrix at $n^{th}$ measurement update time $\xi_n$=measurement noise vector applicable to $n^{th}$ measurement and it is assumed that, in the general case, a number of independent measurements may become available simultaneously.

The optimal utilization of information introduced through a series of measurements of the form given by (11), to estimate the state vector X in a sequential fashion, is the central problem addressed by Kalman estimation theory, and has the following solution. After each measurement (of a sequence of measurements), the estimate of the state, X, is refreshed by the two-step procedure:

$$\hat{X}_n^- = \Phi_n \hat{X}_{n-1} \quad (12)$$

$$\hat{X}_n = \hat{X}_n^- + K_n[y_n - H_n \hat{X}_n^-] \quad (13)$$

where $\hat{X}_n^-$=optimal estimate of vector X just before the $n^{th}$ measurement is processed $X_n$=optimal estimate of vector X immediately after $n^{th}$ measurement is processed $K_n$=Kalman gain matrix at $n^{th}$ measurement update with $K_n$ defined by $$K_n = P_n^- H_n^T (H_n P_n^- H_n^T + R_n)^{-1} \quad (14)$$

in which $P_n^-$=apriori error covariance matrix of vector X $R_n$=measurement noise error covariance matrix and the apriori error covariance matrix, $P_n^-$, is computed from (10) over the interval $t_{n-1}$ to $t_n$.

After processing the $n^{th}$ measurement, the error covariance matrix of the state X is modified to reflect the benefit of incorporating new information introduced by the measurement, by means of:

$$P_n = (I - K_n H_n) P_n^- \quad (15)$$

where $P_n$ is the aposteriori error covariance matrix. The form given by (15) is applicable when the Kalman Filter is fully optimal; that is, when it is a full-state filter in which all components of X are fully accounted for in the mathematical model and, further, are re-estimated after each successive measurement is made available.

In the present invention, after downloading all of the measurements from the various data files within the pig and the magloggers, the post processing routines process the measurements within the Kalman filter in order to estimate system errors, allowing the inertial navigation solution variables to be corrected. The measurements are processed by the Kalman filter, the system errors are estimated, and the inertial navigation solution variables are corrected.

2.2.4.2 KALMAN FILTERING PRACTICE: THE DETERMININATION OF AN ERROR MODEL

An important aspect of defining a Kalman Filter is the specification of the transition and state noise covariance matrices. These matrices are unique for each application, and characterize the dynamics of the system in terms of its response to both constant errors (sensor biases and initial condition errors), and to random forcing functions originating from sensor noise.

The following paragraphs define error models for the various elements in the system suitable for implementing the Kalman Filter used to integrate information from the various subsystems in the pig location application of interest here. The following paragraphs deal with error models for the inertial system, the dead-reckoning system, the odometer measurements, and the logger position measurements.

2.2.4.2.1 ERROR MODEL FOR THE INERTIAL NAVIGATION SOLUTION 810 OF FIG. 8

The solution of (1) and (2) will be imperfect due to errors introduced through the sensor inputs ($\omega$,A); and errors in the initial conditions on C and V. The errors associated with these quantities are defined as the differences between the erroneous solution variables, and their counterparts when the equations are solved with perfect sensors, and exact initial conditions.

The "$\psi$-angle" error model formulation for a strapdown system may be shown to consist of the following set of vector differential equations:

$$\dot{\psi} = -(\rho+\Omega)\times\psi - C\delta\omega + \delta\Omega \quad (21)$$

$$\delta\dot{V} = C\delta A - \psi \times A - (2\Omega+\rho)\times\delta V \quad (22)$$

where $\psi$=attitude error vector $\delta V$=velocity error vector $\delta\omega$=gyro bias error vector $\delta A$=accelerometer bias error vector $\delta\Omega$=earth-rate error vector (used in determining the initial azimuth alignment of the pig)

$\Omega$=earth angular rate vector $\rho$=transport angular rate vector (due to pig translational motion)

A=nongravitational acceleration vector

C=body to local vertical transformation matrix

The attitude and velocity error equations defined by (21) and (22) provide a description of the error propagation characteristics of the strapdown inertial navigation system.

An important subsidiary error equation defines the relationship between the attitude error vector, $\psi$, and the error in the attitude matrix. The relationship is defined by $$\delta C = -\{\psi\} C \quad (23)$$

where $\delta C$ is the error in the attitude matrix.

Another set of error equations required to complete (21) is that associated with the earth-rate error vector, $\delta\Omega$. This error state, which is active only during the initial heading, determination of the pig, is defined by the set of equations $$\delta\Omega = \begin{bmatrix} \delta\Omega_x \\ \delta\Omega_y \end{bmatrix} = 0 \tag{24}$$

where $\delta\Omega_x$ and $\delta\psi_y$ are constant earth-rate errors in a locally level frame that is rotated in azimuth from North by the unknown pig heading at system initialization.

The error vectors, $\delta\omega$ and $\delta A$, in the inertial navigation error equations account for the angular rate and linear acceleration errors originating from errors in the outputs of the inertial sensors. To complete the overall inertial system error model, a model for these errors must be provided.

The errors associated with the inertial sensors may be defined as falling into two categories. The first category, which may be referred to as "sensor-level" errors, are those errors that are not dependent on the sensor's position or orientation in the system. The principal errors that fall into this category are sensor bias, scale-factor, and random drift errors. The remaining errors, which may be referred to as "system-level" errors, arise from misalignments of the sensor input axes when they are assembled into a system. Basic error models applicable to the gyro and accelerometer sensor- and system-level errors are given in the following.

The error in a given gyro's output, due to bias, scale-factor, and random errors is expressed as $$\delta\omega = b_g + k_g\omega + \eta_g \tag{25}$$

where $\delta\omega$=error in measured angular rate
$b_g$=gyro bias error
$\kappa_g$=gyro scale-factor error
$\eta_g$=gyro random drift rate error
$\omega$=angular rate measured by gyro For the pipeline inspection application, the angular rates associated with pig motion are not excessively large, so an adequate representation for the error in the angular rate vector which ignores all gyro scale factor and input-axis misalignments is defined by $$\delta\omega = \begin{bmatrix} b_{g_1} \\ b_{g_2} \\ b_{g_3} \end{bmatrix} + \begin{bmatrix} \eta_{g_1} \\ \eta_{g_2} \\ \eta_{g_3} \end{bmatrix} \tag{26}$$

where the $b_{g_i}$ are the biases associated with the gyro triad, and the $\eta_{g_i}$ are the random gyro errors.

The random uncorrelated noise sequence, $\eta_g$, in the gyro error model is characterized by a standard deviation or, equivalently, by a "random-walk" coefficient. The latter is a commonly used error parameter that applies to the cumulative gyro output angle. The error in the cumulative angle output, due to the random drift rate, $\eta_g$, may be expressed in the form $$\sigma_{74} = K_g t^{1/2}$$

where $\sigma_{74}$ =standard deviation of error in cumulative angle (rad)
$K_g$=random walk coefficient (rad/sec$^{1/2}$)
t=elapsed time (sec)

The random-walk coefficient, $K_g$, expressed in the convenient units of deg/hour$^{1/2}$, is typically used as a measure of the gyro white noise drift The error in a given accelerometer's output, due to bias, scale-factor, and random errors is expressed as $$\delta A = b_a + k_a A + \eta_a \tag{27}$$

where $\delta A$=error in measured angular rate
$b_a$=accelerometer bias error
$k_a$=accelerometer scale-factor error
$\eta_a$=accelerometer random drift rate error
A=nongravitational acceleration measured by accelerometer Since the linear accelerations associated with pig motion are not excessively large for the pipeline inspection application, an adequate representation for the error in the acceleration vector may be accurately approximated by ignoring accelerometer scale factor and input-axis misalignment errors, which results in $$\delta A = \begin{bmatrix} b_{a_1} \\ b_{a_2} \\ b_{a_3} \end{bmatrix} + \begin{bmatrix} \eta_{a_1} \\ \eta_{a_2} \\ \eta_{a_3} \end{bmatrix} \tag{28}$$

where the $b_{a_i}$ are the biases associated with the accelerometer triad, and the $\eta_{a_i}$ are the accelerometer random errors.

As for the gyro, the random uncorrelated error in the accelerometer output is typically defined by a random-walk coefficient characterizing the error in the cumulative output of the sensor. The accelerometer random-walk parameter is usually expressed in the convenient units of ft/sec/hour$^{1/2}$.

2.2.4.2.2 ERROR MODEL FOR DEAD RECKONED POSITION PROCESS 820 OF FIG. 8

The error propagation equation for the dead-reckoned position is derived from the basic dead-reckoning equation defined by (5). Taking the differential of both sides leads to $$\delta\dot{R} = \delta C\dot{s} + C\delta\dot{s} \tag{29}$$

where $\delta R$ is the error in the dead-reckoned position vector and $\delta s$ is the error in pig velocity along the arc length of the trajectory. Substituting for $\delta C$ leads to the expression $$\delta\dot{R} = -\{\psi\}C\dot{s} + C\delta\dot{s} \tag{30}$$

Substituting an explicit expression for $\delta s$ in terms of the odometer scale-factor and boresight errors leads to $$\delta\dot{R} = -\{\psi\}\dot{R} + \dot{s}C\begin{bmatrix} \delta k \\ \delta\alpha \\ \delta\beta \end{bmatrix} \tag{31}$$

The odometer scale factor error, $\delta k$, and boresight errors, $\delta\alpha$ and $\delta\beta$, are defined to be constants and so have the error equation $$\begin{bmatrix} \delta k \\ \delta \alpha \\ \delta \beta \end{bmatrix} = 0 \quad (32)$$

Expressed in terms of components in the Nothl/East/Down frame, the following set of equations results $$\begin{bmatrix} \delta \dot{R}_n \\ \delta \dot{R}_e \\ \delta \dot{R}_d \end{bmatrix} = \begin{bmatrix} 0 & \psi_d & -\psi_e \\ -\psi_d & 0 & \psi_n \\ \psi_e & -\psi_n & 0 \end{bmatrix} \begin{bmatrix} V_n \\ V_e \\ V_d \end{bmatrix} + \begin{bmatrix} f_{11} & f_{12} & f_{13} \\ f_{21} & f_{22} & f_{23} \\ f_{31} & f_{32} & f_{33} \end{bmatrix} \begin{bmatrix} \delta k \\ \delta \alpha \\ \delta \beta \end{bmatrix} \quad (33)$$

where $V_n$, $V_e$, $V_d$ are the velocity components in the NED frame, and the $f_{ij}$ are defined by $$f_{ij} = s c_{ij}$$

A recursive form of the same equation is as follows $$\begin{bmatrix} \delta R_n(i) \\ \delta R_e(i) \\ \delta R_d(i) \end{bmatrix} = \begin{bmatrix} \delta R_n(i-1) \\ \delta R_e(i-1) \\ \delta R_d(i-1) \end{bmatrix} + \begin{bmatrix} 0 & -\Delta R_d & \Delta R_e \\ \Delta R_d & 0 & -\Delta R_n \\ -\Delta R_e & \Delta R_n & 0 \end{bmatrix} \begin{bmatrix} \psi_n \\ \psi_e \\ \psi_d \end{bmatrix} + \quad (34)$$

$$\begin{bmatrix} g_{11} & g_{12} & g_{13} \\ g_{21} & g_{22} & g_{23} \\ g_{31} & g_{32} & g_{33} \end{bmatrix} \begin{bmatrix} \delta k \\ \delta \alpha \\ \delta \beta \end{bmatrix}$$

in which the following definitions apply $$\Delta R_n = \int_{t_{i-1}}^{t_i} V_n dt, \quad \Delta R_e = \int_{t_{i-1}}^{t_i} V_e dt,$$

$$\Delta R_d = \int_{t_{i-1}}^{t_i} V_d dt, \quad g_{ij} = \int_{t_{i-1}}^{t_i} f_{ij} dt$$

2.2.4.2.3 OPTIMAL FILTER 830 AND SMOOTHER 840 ERROR EQUATIONS

The previous discussion has defined the mathematical equations that serve as the basis for defining the transition matrix and state noise covariance matrix required in specifying the Kalman Filter for the pipeline surveying application of interest here.

The error state for the Kalman Filter consists of: 3 attitude error states, 3 velocity error states, 2 earth-rate error states, an odometer scale-factor error state, 2 odometer boresight error states, 3 gyro bias error states, and 3 accelerometer error states. The Kalman Filter state vector can be conveniently defined mathematically as follows:

$$X = (\psi, \delta V, \delta \Omega, \delta k, \delta \alpha, \delta \beta, b_g, b_a)^T$$

The error for the attitude error vector, , and velocity error vector, $\delta V$, are defined by (21) and (22), respectively. The earth rate error vector is defined by (24). The odometer error states are defined by (32), and the gyro and accelerometer bias states by (26) and (28).

The collection of error equations provides the basis for defining the discretized transition matrix, $\Phi$, required in the Kalman Filter, and the state noise covariance matrix, Q.

The optimal smoother defined earlier requires that an error covariance matrix be specified for both the forward and reverse dead-reckoned positions at the $n^{th}$ interior point between two successive loggers. The covariance matrices are determined by carrying out an error analysis of the two applicable relationships, defined by (17) and (18), utilizing the same approach that leads to (31). This results in the following $$\delta x_f(n) = \sum_{j=1}^{n} \left( -\{\psi\} C_j \Delta s_j + (s_j - s_{j-1}) C_j \begin{bmatrix} \delta k \\ \delta \alpha \\ \delta \beta \end{bmatrix} \right) \quad (35)$$

$$\delta x_r(n) = -\sum_{j=M}^{M-n} \left( -\{\psi\} C_j \Delta s_j + (s_j - s_{j-1}) C_j \begin{bmatrix} \delta k \\ \delta \alpha \\ \delta \beta \end{bmatrix} \right) \quad (36)$$

where $\delta x_f(n)$=pig relative position error at the $n^{th}$ interior point between the $(N-1)^{th}$ and $N^{th}$ logger points computed in the forward direction $\delta x_r(n)$=pig relative position error at the $n^{th}$ interior point between the $(N-1)^{th}$ and $N^{th}$ logger points computed in the reverse direction M=number of interior points between the two loggers at which pig attitude and odometer data are available $\hat{C}_j$=best estimate of attitude matrix after optimal filtering $\Delta \hat{s}_j$=best estimate of incremental pig travel after application of the correction for the estimated odometer scale-factor and boresight errors and it is assumed that the components of the attitude error vector, $\psi$, are constant over the logger interval, which is very reasonable given the very low rate of change of this vector. Note also the implicit assumption that the odometer scale factor and boresight errors are constant over the logger interval. This will always be true because these parameters are estimated during a preliminary pass through the data, and then used in a subsequent pass entailing the smoothing operation. Therefore, the errors in the odometer parameters will be constant, with the same values over all logger intervals. The error covariance matrices for the forward and reverse dead-reckoned positions are derived directly from (35) and (36), and take the form $$P_f(n) = E[\delta x_f(n) \delta x_f^T(n)] = M_f(n) E(zz^T) M_f^T(n) = M_f(n) p(N) M^T_f(n) \quad (37)$$

$$P_r(n) = E[\delta x_r(n) \delta x_r^T(n)] = M_r(n) E(zz^T) M_r^T(n) = M_r(n) p(N) M_r^T(n) \quad (38)$$

where the error vector, z, consists of the three attitude errors and the three odometer errors, all being evaluated at the $N^{th}$ logger position or, explicitly $$z = (\psi_n, \psi_e, \psi_d, \delta k, \delta \alpha, \delta \beta)^T$$

with the matricies $M_f(n)$ and $M_r(n)$ being evaluated numerically from the error expressions (35) and (36), and the matrix, p(N), being defined as error covariance matrix of the error vector, z.

2.2.5 SUBTRACTING ERRORS FROM THE DATA FILE VALUES: THE OPTIMAL SMOOTHER—840

Referring again to FIG. 8, once the best estimate of the pig attitude matrix 812 is known as a function of time over a given logger interval, and estimates are available for the odometer scale-factor and boresight errors, the dead-reckoned position computation over the logger interval may be repeated. The dead-reckoning starts from a precisely known position at the $(N-1)^{th}$ logger and terminates at a second precisely known position at the $N^{th}$. logger.

Generally, due to errors which remain in the information being processed, the computed position upon reaching the $N^{th}$ logger will differ from the known position. The dead-reckoned pig position can then be determined in the reverse direction starting from the precisely known $N^{th}$.logger position and ending at the (N−1)th logger position. The smoothing process, which blends the dead-reckoned position obtained in the forward direction with that obtained in the reverse direction, removes the systematic contributions from the attitude matrix error and the odometer scale-factor and boresight errors. The resultant pig position represents the best estimate of the pig at all of the interior points between each pair of precisely known logger reference points. This operation is carried out as each logger point is reached in succession.

Continuing to refer to FIG. 8, the function of the Optimal Smoothing Module 840 is to refine the knowledge of the pig's position in the segment of the pipeline between loggers, using all information that is available over the whole logger interval. The concept of smoothing is applicable in situations where post-processing is involved, and leads to an improved estimate of the state vector over some fixed interval, relative to that which results from the filtering activity alone. The reason for the improved accuracy is that filtering produces an estimate of the state at each point in time, using measurements occurring only up to that time; whereas, smoothing produces a revised estimate of the state at each point, based also on measurements that occurred after that time.

A number of smoothing concepts have been suggested since the introduction of the Kalman Filter in the earlier 60's. A fairly simple and effective concept for smoothing used in the present study is defined as follows. First, from estimation theory, the best estimate of a quantity (in this case the state vector), given two estimates $\hat{x}_1$ and $\hat{x}_2$ with covariance matrices $P_1$ and $P_2$ respectively, is given by:

$$\hat{x}=(P_1^{-1}+P_2^{-1})^{-1}(P_1^{-1}\hat{x}_1+P_2^{-1}\hat{x}_2) \quad (16)$$

where x is the best combined estimate.

It the present application the estimate $\hat{x}_1$ is that which derives from forward inertial navigation, and the estimate $\hat{x}_2$ is that which derives from the reverse inertial navigation.

In the pipeline inspection application, the two sets of estimates consist of the dead-reckoned position determined first in the forward direction from the $(N-1)^{th}$ logger position to the $N^{th}$ logger position, and then in the reverse direction from the $N^{th}$ logger position to the (N−1)th logger The two sets of estimates are computed from $$x_f(n) = X(N-1) + \sum_{j=1}^{n} \hat{C}_j \Delta \hat{s}_j \quad (17)$$

$$x_r(n) = X(N) - \sum_{j=M}^{M-n} \hat{C}_j \Delta \hat{s}_j \quad (18)$$

where $x_f(n)$=pig position vector relative to the $(N-1)^{th}$ logger point at the $n^{th}$ interior point between the $(N-1)^{th}$ and $N^{th}$ logger points computed in the forward direction $x_r(n)$=pig position vector relative to the $(N-1)^{th}$ logger point at the $n^{th}$ interior point between the $(N-1)^{th}$ and $N^{th}$ logger points computed in the reverse direction X(N−1)=position vector of the $(N-1)^{th}$ logger X(N)=position vector of the $N^{th}$ logger M=number of interior points between the two loggers at which pig attitude and odometer data are available (typically at spacings of a fraction of a meter)

$\hat{C}_j$=best estimate of attitude matrix after optimal filtering $\Delta \hat{s}_j$=best estimate of incremental pig odometer output vector after application of the correction for the estimated odometer scale-factor and boresight errors In addition to the forward and reverse position estimates defined above, the smoothing algorithm requires the error covariance matrices $P_f(n)$ and $P_r(n)$ for the forward and reverse estimates, respectively. The error covariance matrices for the forward and reverse dead-reckoned position vectors are defined at the $n^{th}$ interior point between two successive loggers as $$P_f(n)=E[\delta x_f(n)\delta x_f^T(n)]=M_f(n)p(N)M_f^T(n) \quad (19)$$

$$P_r(n)=E[\delta x_r(n)\delta x_r^T(n)]=M_r(n)p(N)M_r^T(n) \quad (20)$$

where E denotes the expected value, $\delta x_f$ and $\delta x_r$ are the respective errors in the forward and reverse dead-reckoned positions, with the matrices p(N), $M_f$ and $M_r$ being explicitly defined in the subsequent discussion.

Referring again to FIG. 8, at a step corresponding to an inertial navigation process 810, data previously obtained by the gyros and accelerometers of the inspection apparatus 302 are analyzed by the inertial navigation process 810 to obtain an inertial navigation solution, comprising an attitude matrix 812 and a velocity vector 822. The inertial navigation solution provides the attitude and velocity of the pig at each clock interval. The attitude matrix 812, describes the transformation of vectors from a reference frame having an alignment corresponding to the inspection apparatus 302 relative to a North/East/Down coordinate frame having an alignment corresponding to the reference location.

Within the inertial navigation solution process 810, the IMU, gyro, and accelerometer data are integrated to provide an inertial navigation solution in the north/east/down frame consisting of an attitude matrix and a three dimensional velocity vector. The attitude matrix is a 3×3 (9 element matrix) having elements equal to the cosines of various attitude angles. As will be understood by one skilled in the art, the orientation of the pig at each point in time may described in terms of orientation angles, between the center line of the pig and a reference direction in inertial space. Each gyro output consists of a sequence of incremental attitude angles, and each accelerometer output consists of a sequence of incremental velocities.

Referring again to FIG. 8, at a step corresponding to a dead reckoning process 820, the attitude matrix and the results of the odometer measurements 304 obtained from the recorder 316 of the inspection apparatus 302 is received and analyzed. The dead reckoning process 820 determines a three-dimensional position vector (in North/East/Down coordinates) The dead reckoning process 820 produces an estimate of a position vector 822. The position vector 822 is provided to the inertial navigation solution process 810 to allow the earth-rate components to be computed.

Within the dead reckoning process 820, the attitude information derived in the inertial navigation solution (i.e. the attitude matrix and the three dimensional velocity vector) are combined with the odometer data collected and stored during the real time phase of the survey to derive pig position at all points in the pipeline network. Each of the instantaneous increments of pig travel along the arc of the pipeline during each small time interval using the instantaneous attitude matrix obtained from the inertial navigation solution process 810, is resolved to determine the increment of pig travel in a North/East/Down reference frame. The dead reckoning process 820 also sums these increments to determine the pig position coordinates in a North/East/Down reference frame.

As can be appreciated by reference to FIG. 8, the velocity vector 814 and position vector 822 are obtained from data recorded purely on the inspection apparatus 302. However, the inertial navigation solution process 810 and the dead reckoning position determination process 820, are executed offline within the post processing 800.

Referring again to FIG. 8, at a step corresponding to an optimal filtering process 830 the off-site computer 400 analyzes the position vector 822, velocity vector 814, and odometer measurement 802 in light of logger position information. As described above, logger position data is obtained from an analysis of the two GPS data points for each logger (i.e. The GPS data recorded at step 612 and GPS data simultaneously recorded at the reference location), as well as the intended information obtained from the survey. A highly precise estimate of logger position is therefore obtained in global positioning satellite reference frame, in terms of longitude, and latitude and altitude (i.e., depth).

The optimal filter step 830 provides a best estimate of various errors 830 including pig attitude matrix error and odometer scale factor error, and a boresight error.

Once the various estimates are determined, these error estimates are used by an optimal smoother process 830 to determine a best estimate of pig position at each point in time.

Within the optimal filter process 830, error sources are calculated. Sensor biases, odometer scale factor, and boresight errors are all estimated using Kalman filtering techniques. Both the logger reference position and the odometer are used. The optimal filter produces corrections to the pig attitude matrix and velocity vector, and an estimate of the odometer scale factor and bore side errors.

Referring again to FIG. 8, within the optimal smoother 840 once the best estimate of the pig attitude matrix is known as function of time over a given logger interval, and once estimates are available for the odometer scale factor and boresight errors, the dead reckoning position computation over the logger interval is repeated. The optimal smoother performs the same steps as the dead reckoning process 820, with the error estimate being subtracted from the data.

In other words, the optimal smoother 840 uses the results of the optimal filter 830, and repeats certain steps already performed, albeit on corrected data. As stated above, the optimal filter 830 produces the best estimate of sensor biases, odometer scale factor errors, and boresight errors, and stores these estimates in File 5 (shown in FIG. 8). The optimal smoother 840 performs a number of steps on the data, using the error estimates in File 5 to correct the data before executing each step—the optimal smoother 840 subtracts known errors from the data, thereby "correcting" the data (see equation 16). At step 844, the optimal smoother re-executes the dead-reckoning process equations for the corrected data (see equation 17). At step 846, the optimal smoother reverses the order of the data to simulate the pig moving in a reverse direction through the pipeline, and then re-executes the dead-reckoning process equations for the corrected data in the reverse direction (see equation 18).

Equations 17 and 18 are dead-reckoning equations, using $\hat{C}$ (i.e., the attitude matrix corrected for errors stored in File 5) rather than C for the attitude matrix, and using $\Delta\hat{s}$ (i.e., the best estimate of odometer incremental travel, corrected for odometer and boresight errors). Equation 17 uses the forward direction data, while Equation 18 uses the same data but in a reverse direction. The forward and reverse directions are then combined to produce an optimal estimate of position vector at each moment of time, which is stored in File 6.

Referring now to FIG. 9, a chart showing an exemplary output file is presented. The chart includes one row or record for each defect or anomaly encountered. The first column 902 and the second column 904 collectively provide the location of the defect in a format useful to a repair team that does not have access to a GPS receiver. In the prior art, without GPS, location within the pipeline was reported as a number of welds and a distance from the previous weld. For example, "ten inches past weld #503" was useful in locating a point of interest along the pipeline. A repair team would "walk the pipeline," measuring out the distance until weld #503 was found, and then measure along the weld section an additional ten inches. Consequently, the first two columns of the chart in FIG. 9 provide this information. The first column 902 provides the girth weld count measured from the launch, and the second column 904 provides the distance from the last girth weld to the feature of interest, e.g. a defect. For example, in the first row shown in FIG. 9, a feature of interest is found 1.1 meter from girth weld 1.

In a third column 906, the absolute distance between the defect and the insertion point along the pipeline 100 is indicated. The absolute distance is the distance measured by the odometer, not from any particular girth weld but from the beginning of the pipeline, i.e. the pint at which the pig was inserted into the pipeline. In other words, the third column merely accumulates the odometer readings from the launch point to the point of interest. The fourth column 908 identifies the feature of interest. If a defect is encountered during a field run, the type of defect, as well as whether the defect is internal or external to the pipeline, is provided in the fourth column, as well as additional comments. When such information is not available, the entry in column 908 is blank.

In the fifth column 910, the type of defect detected is mapped to an explanatory comment understandable to a repair team. The type of defect allows the repair team to prepare for the necessary repair. In the sixth column 912, the magnitude of the magnetic sensor output detected at the defect location by the defect inspection sensor 312 is indicated. In the seventh column 914, the longitudinal axis length of the defect is indicated, in millimeters. In the eighth column 916, the percent of the pipeline section that is damaged is indicated.

In the ninth column 918, the orientation of the defect location is indicated, in degrees and minutes, is indicated. The orientation is provided in hours and minutes. The cross section of the pipeline may be regarded as a dial of a wristwatch or clock, with "12 o'clock" representing the top of the pipeline cross section and "6 o'clock" representing the bottom. The sense-direction is as viewed in the direction of the flow through the pipeline, to distinguish 3 o'clock from 9 o'clock. The orientation of the defect is particularly necessary when the defect is to be found on the internal surface of the pipeline, invisible to visual inspection of the external surface.

The remaining columns of 920–924 of the chart indicate defect location in a North/East/Down coordinate system, giving longitude, latitude, and depth of the defect location. The longitude and latitude are reported in degrees, minutes, and seconds, unless a user commands an alternate output format. The depth is provided in meters, unless an alternate format is commanded. One alternate format that a user may command is from a particular reference point, such as the launch point. Another alternate format is to provide the location of each feature of interest in units of distance, such as meters north, meters east, and meters down from the launch point. Other formats will be readily apparent upon examination of the above description.

The foregoing disclosure and description of the invention are illustrative and explanatory thereof, and various changes in the details of the illustrated apparatus and construction and method of operation may be made without departing from the spirit of the invention.

What is claimed is:

1. A system for inspecting a pipeline and for mapping a defect within the pipeline, the system comprising:
   a pig insertable within the pipeline, the pig having a kinematic property sensor generating kinematic property sensor data and a defect/anomaly inspection unit generating defect/anomaly inspection data, the kinematic property sensor having unknown initial conditions;
   a maglogger at a known location external to and in close proximity with the pipeline, the maglogger containing a device for detecting the passage of the pig along the pipeline, the maglogger generating maglogger data; and
   a computer system configured to receive maglogger data and kinematic property sensor data, and to combine maglogger data with kinematic property sensor data to derive the location of the detected defects and to determine initial conditions of the kinematic property sensor.

2. The system of claim 1, wherein: the kinematic property sensor comprises an inertial measurement unit for detecting accelerations of the pig, the inertial measurement unit containing a plurality of accelerometers triad and a plurality of gyroscopes.

3. The system of claim 1, wherein: the kinematic property sensor comprises an odometer apparatus for detecting distance traveled by the pig.

4. The system of claim 1, wherein:
   the defect/anomaly inspection unit comprises a magnetic sensor for detecting anomalies of the pipeline.

5. The system of claim 1, wherein:
   the computer system is further configured to process received maglogger data and kinematic property sensor data in a reverse chronological order, such that data received after the pig passed a given point along the pipeline are processed before data received before the pig passed the given point.

6. The system of claim 1, wherein:
   the pig further includes a first clock, such that each kinematic property sensor datum is time-stamped;
   the maglogger further includes a second clock, such that the maglogger datum indicating the passage of the pig along the pipeline is time-stamped, the second clock further being synchronized to the first clock;
   the computer system is configured to correlate maglogger data with kinematic property sensor data, the computer system further configured to generate an error model identifying errors in the kinematic property sensor.

7. The system of claim 6, wherein:
   the computer system is further configured to combine the error model with the received with kinematic property sensor data, to generate improved kinematic data.

8. The system of claim 1, wherein:
   the computer system is configured to process received data multiple times, including a first process in which the data is processed in a forward chronological order to derive a first error model and a first set of initial conditions, a second process in which the data is processed in a reverse chronological order to derive a second error model and a second set of initial conditions, and a third process in combination with the first and second error models and the first and second sets of initial conditions to derive an improved identification of the location of the detected defects.

9. The system of claim 8, wherein the computer system processes contain Kalman filters.

10. A system for inspecting a pipeline and for mapping a defect within the pipeline, the system comprising:
    a fixed location sensor in proximity to the pipeline, the fixed location sensor for providing a reference location in a terrestrial coordinate frame;
    a pipeline pig vehicle having a defect sensor device for determining the location of defects in the pipeline in a second coordinate frame;
    a kinematic device mounted with the defect sensor device, the kinematic device for measuring the relationship between the second coordinate frame and the terrestrial coordinate frame, the kinematic device having an initially unknown orientation in the second coordinate frame;
    a computer system configured to receive the reference location, to receive the location of defects in the pipeline, and to receive the relationship between the second coordinate frame and the terrestrial coordinate frame, the computer system further configured to transform the location of defects in the pipeline into the terrestrial coordinate frame with respect to the reference location using signals from global positioning satellites.

11. The system of claim 10, wherein said fixed location sensor further comprises:
    a maglogger external to and in close proximity with the pipeline, the maglogger having a global positioning satellite receiver for receiving signals from global positioning satellites such that the location of the maglogger is ascertainable in a terrestrial coordinate frame.

12. The system of claim 11, the fixed location sensor comprising:
    a reference receiver, the reference receiver having a global positioning satellite receiver for providing the reference location in the terrestrial coordinate frame;
    the second coordinate frame comprising:
       a pipeline pig-originated coordinate frame;
    the kinematic device comprising:
       an inertial measurement unit for measuring the relationship between the pipeline pig-originated coordinate frame and an inertial frame;
    at least one of the maglogger and the computer system comprising:
       a device for defining the relationship between the inertial frame and the terrestrial coordinate frame.

13. The system of claim 12, wherein:
    the terrestrial coordinate frame is a north/east/down coordinate frame, the device for defining the relationship between the inertial frame and the terrestrial coordinate frame including a device for compensating for the curvature of the earth.

14. The system of claim 12, wherein:

the inertial measurement unit is a strap-down inertial measurement unit mounted on the pig, the inertial measurement unit containing a triad of accelerometers and a triad of gyroscopes, the inertial measurement unit measuring the relationship between the pig-originated coordinate frame and an inertial frame;

the device for defining the relationship between the inertial frame and the terrestrial coordinate frame including a device for compensating for the curvature of the earth.

15. The system of claim 10, wherein:

the computer system is configured to provide the location of defects in the pipeline into the terrestrial coordinate frame with respect to the reference location in a north/east/down coordinate frame, such that any detected defect in the pipeline may be located as a distance north of the reference location, a distance east of the reference location, and a depth below the earth's surface.

16. The system of claim 10, further comprising:

an odometer apparatus, mounted with the kinematic device and the sensor device, the odometer apparatus for measuring the overall curvolinear distance traveled by the odometer apparatus, the odometer apparatus further configured to provide odometer data to the computer system.

17. The system of claim 11, the kinematic device comprising:
an inertial measurement unit;
further comprising:
an odometer apparatus, mounted with the kinematic device and the defect sensor device, the odometer apparatus for measuring the overall curvilinear distance traveled by the odometer apparatus, the odometer apparatus further configured to provide odometer data to the computer system, computer system comprising:
a data port, the data port configured to:
receive data from the maglogger;
receive data from the odometer apparatus, the odometer apparatus data identifying a location in the second coordinate frame;
receive data from the inertial measurement unit, the inertial measurement unit data twice-integratable to identify a location in the second coordinate frame, the inertial measurement unit relating the second and terrestrial coordinate frames;
a navigation solver configured to receive inertial measurement unit data and to generate an attitude matrix and a velocity vector for each inertial measurement unit datum;
a filter, the filter configured to associate a maglogger datum and an odometer datum with each attitude matrix and with each velocity vector, the filter providing an error model corresponding to the odometer and an error model corresponding to the inertial measurement unit;
a smoother coupled to the filter within the computer system, the smoother configured to remove errors from the attitude matrices, the smoother processing the attitude matrices in a forward direction and also processing the attitude matrices in a reverse direction; and
a transformer, the transformer coupled to receive attitude matrices from the smoother and further coupled to receive the location of the defects, the transformer configured to transform the location of defects in the pipeline into a terrestrial coordinate frame with respect to the reference location using signals from global positioning satellites.

18. A pig for insertion into a fluid-carrying pipeline, the pig comprising:

a pig body;

a defect sensor, the defect sensor configured to receive an assertable signal and further configured to generate data when the signal is asserted; and an odometer apparatus, having a wheel rotatably mounted on the pig body, the wheel configured to be urged against the interior of the pipeline, the wheel having a fine-pitch castillation, the odometer apparatus configured to assert the signal when the wheel is in any of a first set of predefined orientations with respect to the pig body and further configured not to assert the signal when the wheel is in any of a second set of predefined orientations with respect to the pig body, such that the assertion of the signal is substantially dependent on the distance traveled relative to the pipeline and substantially independent of pig speed relative to the pipeline.

19. The pig of claim 18, further comprising:

a clock configured to generate a clock signal indicative of elapsed time; a scan assembler configured to receive the clock signal, the scan assembler further being configured to be triggered by assertion of the odometer signal, the scan assembler further being configured to time-stamp data from the sensor with a representation of the elapsed time.

20. The pig of claim 19, further comprising:

a kinematic sensor for measuring kinematics of the pig in a first coordinate system, the kinematic sensor being configured to provide kinematic data to the scan assembler for time-stamping.

21. The pig of claim 20, wherein:

the kinematic sensor comprises an inertial measurement unit, the first coordinate system being an inertial reference frame.

22. A method for inspecting a pipeline and for mapping a defect within the pipeline, the method comprising steps of:

inserting a pig within the pipeline, the pig having a kinematic property sensor generating kinematic property sensor data and a defect/anomaly inspection unit generating defect/anomaly inspection data, such that the pig is carried along with the fluid in the pipeline;

placing a maglogger at a known location external to and in close proximity with the pipeline, the maglogger containing a device for detecting the passage of the pig along the pipeline, the maglogger generating maglogger data;

while the pig is being carried along with the fluid in the pipeline, recording within the pig both the kinematic property sensor data and the defect/anomaly inspection data;

when the pig is within a predetermined distance from the maglogger or has a predetermined speed with respect to the maglogger, recording maglogger data within the maglogger;

recovering data from the pig;

downloading kinematic property sensor data from the pig and maglogger data from the maglogger to a computer system;

determining an initial orientation of the kinematic property sensor from the kinematic property sensor data downloaded in the downloading step;

combining the maglogger data with the kinematic property sensor data to derive an improved estimate of the location of the pig;

combining the defect/anomaly inspection data with the improved estimate of the location of the pig to determine an improved estimate of the location of detected defects.

23. The method of claim 22, wherein:

the step of recording the kinematic property sensor data within the pig further includes a step of detecting accelerations of the pig using an inertial measurement unit containing an orthogonal accelerometer triad and an orthogonal gyroscope triad.

24. The method of claim 22, wherein:

the step of recording the kinematic property sensor data within the pig further includes a step of detecting distance traveled by the pig using an odometer apparatus.

25. The method of claim 24, wherein:

the step of recording the defect/anomaly inspection data within the pig includes a step of detecting physical aspects of the pipeline using a magnetic sensor.

26. The method of claim 22, further comprising a step of:

processing received maglogger data and kinematic property sensor data in a reverse chronological order, such that data received after the pig passed a given point along the pipeline are processed before data received before the pig passed the given point.

27. A system for inspecting a pipeline and for mapping a defect within the pipeline, the system comprising:

a pig insertable within the pipeline, the pig having an on-board real-time sensor generating on-board real-time sensor data during a traversal of the pipeline, the on-board real-time sensor data indicative of instantaneous pig location;

a first off-board real-time sensor located external to the pig and to the pipeline, the first off-board real-time sensor configured to measure data pertaining to the pig during the traversal of the pipeline; a computer system for receiving data from the on-board real-time sensor and the off-board real-time sensor, the computer system configured to combine the data to produce improved data; and a second off-board real-time sensor, the first and the second off-board real-time sensors being within a set of off-board real-time sensors, such that each of the set of off-board real-time sensors uses global positioning satellite-derived position data, the computer system configured to allow on-board sensor data to be corrected by comparison with the off-board real-time sensor data and further configured to determine pig position between the first and the second off-board real-time sensors according to a dead-reckoned positioning process.

28. The system of claim 27, wherein:

the on-board real-time sensor is an inertial measurement unit;

the first off-board real-time sensor is a maglogger; and the computer system is a post-processing computer system.

29. A method for determining the location of a pipeline pig within a pipeline, the method comprising the steps of:

measuring a direction of travel over a period of time;

measuring incremental distance traveled over the period of time; and integrating the distance and the direction of travel to determine the location of the pipeline pig, the step of integrating the distance and the direction including steps of:

multiplying a scalar quantity representing incremental distance traveled by a vector quantity representing direction to provide an incremental directed change in position over the period of time; and integrating the incremental directed change in position, with respect to an initial position of the pig, to provide the position of the pig within the pipeline.

30. The method of claim 29, wherein:

the step of measuring a direction of travel includes a step of measuring the direction of travel in more than one direction; and the step of measuring incremental distance traveled over the period of time includes a step of measuring distance in more than one direction.

31. The method of claim 30, wherein:

the step of measuring a direction of travel includes a step of measuring the relative orientation of a direction vector with respect to an earth reference frame.

32. The method of claim 35, wherein:

the step of measuring a direction of travel includes a step of providing a transformation matrix, the transformation matrix describing a relationship between a reference frame oriented along an instantaneous orientation of the pig and the earth reference frame.

* * * * *

UNITED STATES PATENT AND TRADEMARK OFFICE
CERTIFICATE OF CORRECTION

PATENT NO. : 6,243,657 B1  
DATED : June 5, 2001  
INVENTOR(S) : Alan Tuck et al.

Page 1 of 1

It is certified that error appears in the above-identified patent and that said Letters Patent is hereby corrected as shown below:

<u>Title page,</u>
Assignee, should read:
-- PII North America, Inc., Houston, TX (US) and Honeywell, Inc., Minneapolis, MN (US) --.

Signed and Sealed this

Fifth Day of February, 2002

Attest:

JAMES E. ROGAN
*Attesting Officer*     *Director of the United States Patent and Trademark Office*